United States Patent
Benson et al.

(10) Patent No.: US 12,427,479 B2
(45) Date of Patent: Sep. 30, 2025

(54) SYSTEMS FOR ISOLATION AND/OR SEPARATION OF PRODUCTS FROM PRODUCTION PROCESSES

(71) Applicant: Smartflow Technologies, Inc., Sanford, NC (US)

(72) Inventors: Todd Benson, Sanford, NC (US); Kim Davis, Sanford, NC (US); Jason Bell, Sanford, NC (US); James Kacmar, Sanford, NC (US)

(73) Assignee: SMARTFLOW TECHNOLOGIES, INC., Sanford, NC (US)

( * ) Notice: Subject to any disclaimer, the term of this patent is extended or adjusted under 35 U.S.C. 154(b) by 0 days.

(21) Appl. No.: 18/464,379

(22) Filed: Sep. 11, 2023

(65) Prior Publication Data

US 2024/0042390 A1 Feb. 8, 2024

Related U.S. Application Data

(60) Division of application No. 17/089,893, filed on Nov. 5, 2020, now Pat. No. 11,839,856, which is a division of application No. 15/922,360, filed on Mar. 15, 2018, now Pat. No. 10,894,232, which is a division of application No. 14/867,084, filed on Sep. 28, 2015, now Pat. No. 9,937,469, which is a continuation of application No. 13/985,367, filed as application No. PCT/US2012/025874 on Feb. 21, 2012, now Pat. No. 9,163,265.

(60) Provisional application No. 61/445,010, filed on Feb. 21, 2011.

(51) Int. Cl.
| | |
|---|---|
| *B01D 61/14* | (2006.01) |
| *B01D 61/02* | (2006.01) |
| *B01D 63/08* | (2006.01) |
| *C10G 31/09* | (2006.01) |
| *C10L 1/02* | (2006.01) |
| *C10L 1/18* | (2006.01) |
| *C12M 1/00* | (2006.01) |
| *C12M 1/12* | (2006.01) |
| *C12P 5/02* | (2006.01) |
| *C12P 7/06* | (2006.01) |
| *C12P 7/10* | (2006.01) |
| *C12P 7/14* | (2006.01) |

(52) U.S. Cl.
CPC ......... *B01D 61/145* (2013.01); *B01D 61/027* (2013.01); *B01D 61/147* (2013.01); *B01D 63/08* (2013.01); *B01D 63/082* (2013.01); *C10G 31/09* (2013.01); *C10L 1/023* (2013.01); *C10L 1/026* (2013.01); *C10L 1/1802* (2013.01); *C12M 21/12* (2013.01); *C12M 47/10* (2013.01); *C12P 7/06* (2013.01); *C12P 7/10* (2013.01); *C12P 7/14* (2013.01); *B01D 2311/04* (2013.01); *B01D 2311/06* (2013.01); *B01D 2311/2626* (2013.01); *B01D 2311/2669* (2013.01); *B01D 2311/2688* (2013.01); *C10G 2300/1014* (2013.01); *C10G 2300/302* (2013.01); *Y02E 50/10* (2013.01); *Y02P 30/20* (2015.11)

(58) Field of Classification Search
None
See application file for complete search history.

(56) References Cited

U.S. PATENT DOCUMENTS

| | | | |
|---|---|---|---|
| 4,578,353 A | 3/1986 | Assarsson et al. | |
| 4,867,876 A | 9/1989 | Kopf | |
| 4,882,050 A | 11/1989 | Kopf | |
| 4,956,085 A | 9/1990 | Kopf | |
| 5,034,124 A | 7/1991 | Kopf | |
| 5,049,268 A | 9/1991 | Kopf | |
| D322,117 S | 12/1991 | Kopf | |
| D323,202 S | 1/1992 | Kopf | |
| D324,720 S | 3/1992 | Kopf | |
| D325,070 S | 3/1992 | Kopf | |
| D327,313 S | 6/1992 | Kopf | |
| D328,789 S | 8/1992 | Kopf | |
| 5,232,589 A | 8/1993 | Kopf | |
| 5,342,517 A | 8/1994 | Kopf | |
| 5,360,555 A | 11/1994 | Batten | |
| 5,372,722 A * | 12/1994 | Schwering | B01D 65/02 210/636 |
| D357,059 S | 4/1995 | Kopf | |
| 5,543,050 A | 8/1996 | Roshanravan | |
| 5,593,580 A | 1/1997 | Kopf | |
| 5,730,029 A | 3/1998 | Stoldt et al. | |
| 5,868,930 A | 2/1999 | Kopf | |
| 6,022,742 A | 2/2000 | Kopf | |

(Continued)

FOREIGN PATENT DOCUMENTS

| | | |
|---|---|---|
| EP | 0364545 A1 * | 4/1990 |
| WO | WO2011088373 A1 | 7/2011 |

OTHER PUBLICATIONS

Tyson K. Shaine. "Brown Grease Feedstocks for Biodiesel." National Renewable Energy Laboratory Jun. 19, 2002.
Galitsky, Christina et al. "Energy Efficiency Improvement and Cost Saving Opportunities for the Corn Wet Milling Industry." Ernest Orlando Lawrence Berkeley National Laboratory Jul. 2003.
Mittelbach, Martin. "Biodiesel: Production Technologies and Perspectives." Institute for Chemistry (IFC) Working Group Renewable Resources Karl-Franzens-University Graz A-0810 Graz Austria Sep. 19, 2005.

(Continued)

*Primary Examiner* — Michelle F. Paguio Frising
(74) *Attorney, Agent, or Firm* — Casimir Jones, S.C.; Tristan A. Fuierer

(57) ABSTRACT

The present invention relates to separation of desired target products from biological, plant, and waste-type material, wherein the desired target products include renewable fuels such as ethanol, biobutanol, and biodiesel, wherein the separation is conducted with a cross-flow filtration system having the ability to separate desired products from both non-viscous and viscous medium.

1 Claim, 9 Drawing Sheets

(56) References Cited

U.S. PATENT DOCUMENTS

| | | | |
|---|---|---|---|
| 6,048,727 | A | 4/2000 | Kopf |
| 6,139,746 | A | 10/2000 | Kopf |
| 6,214,221 | B1 | 4/2001 | Kopf |
| 6,214,574 | B1 | 4/2001 | Kopf |
| 6,383,380 | B1 | 5/2002 | Kopf |
| 6,464,875 | B1 | 10/2002 | Woodruff |
| 6,569,340 | B2 | 5/2003 | Kopf |
| 6,596,172 | B1 | 7/2003 | Kopf |
| 6,827,960 | B2 | 12/2004 | Kopf et al. |
| 6,852,352 | B2 | 2/2005 | Kopf et al. |
| 6,875,459 | B2 | 4/2005 | Kopf et al. |
| 6,946,075 | B2 | 9/2005 | Kopf |
| 7,384,562 | B2 | 6/2008 | Rogers |
| 7,544,296 | B2 | 6/2009 | Kopf et al. |
| 7,632,319 | B2 | 12/2009 | Rogers |
| 7,732,173 | B2 | 6/2010 | Mairal et al. |
| 7,767,839 | B2 | 8/2010 | Berry et al. |
| 7,806,957 | B1 | 10/2010 | Burke |
| 8,366,794 | B2 | 2/2013 | Tremblay et al. |
| 9,163,265 | B2 | 10/2015 | Benson |
| 9,937,469 | B2 | 4/2018 | Benson |
| 10,005,697 | B1 | 6/2018 | Vander Hoff et al. |
| 11,839,856 | B2 | 12/2023 | Benson et al. |
| 2002/0158024 | A1 | 10/2002 | Van Slyke et al. |
| 2003/0232109 | A1 | 12/2003 | Dawley et al. |
| 2004/0025715 | A1 | 2/2004 | Bonde et al. |
| 2004/0139864 | A1* | 7/2004 | Kopf .............. B01D 61/145 99/495 |
| 2005/0023220 | A1 | 2/2005 | Barak et al. |
| 2006/0004237 | A1 | 1/2006 | Appel et al. |
| 2006/0283221 | A1 | 12/2006 | Camisa |
| 2007/0119771 | A1 | 5/2007 | Schukar et al. |
| 2007/0199894 | A1 | 8/2007 | Peyton et al. |
| 2008/0057553 | A1 | 3/2008 | Cadwalder |
| 2008/0296237 | A1 | 12/2008 | Hammond |
| 2009/0017164 | A1 | 1/2009 | Schisler et al. |
| 2010/0055753 | A1 | 3/2010 | Geros |
| 2011/0252696 | A1* | 10/2011 | Franklin .............. C10G 3/52 44/388 |
| 2011/0275845 | A1 | 11/2011 | Woods et al. |
| 2012/0205311 | A9 | 8/2012 | Kopf et al. |
| 2013/0015119 | A1 | 1/2013 | Pugh et al. |
| 2013/0115588 | A1 | 5/2013 | Davis et al. |
| 2013/0212932 | A1 | 8/2013 | Bell et al. |
| 2013/0236938 | A1 | 9/2013 | Vander Hoff et al. |
| 2021/0113966 | A1 | 4/2021 | Benson et al. |

OTHER PUBLICATIONS

Paynich Mallory. "Transesterification of Vegetable Oils to Produce Biodiesel Fuel." MMG445 eJournal 2005.

Chakrabarti Alicia R. et al. "4Waste Grease Biodiesel Production at a Wastewater Treatment Plant." WEFTEC®08 2008 pp. 2770-2789.
Drapcho, Caye M et al. "Biofuels Engineering Process Technology." 2008 The McGraw-Hill Companies, Inc.
Durrett Timothy P. "Plant triacylglycerols as feedstocks for the productions of biofuels." The Plant Journal (2008) vol. 54 pp. 593-607.
Sheedlo, Michael. "A review of the processes of biodiesel production." MMG 445 Basic Biotechnology eJournal 2008, 4:61-65.
Fjerbaek, Lene et al. "A Review of the Current State of Biodiesel Production Using Enzymatic Transesterification." Biotechnology and Bioengineering vol. 102, No. 5, Apr. 1, 2009.
Wiman, M. et al. "Rheological Characterization of Dilute Acid Pretreated Softwood." Biotechnology and Bioengineering EPub Dec. 2010 vol. 108 pp. 1031-1041.
Kawakami, Koei et al. "Application of a Burkholderia cepacia lipase-immpbilized silica monolith to batch and continuous biodiesel production with a stoichiometric mixture of methanol and Jatropha oil." Biotechnology for Biofuels 2011, 4:42.
Luković, Nevena et al. "Biodiesel Fuel Production by Enzymatic Transesterification of Oils: Recent Trends Challenges and Future Perspectives." Alternative Fuel, 2011, pp. 47-72.
Stockinger, Herman. "Converting Waste to BioDiesel." World Biofuels Markets 2011, Rotterdam, Mar. 24, 2011.
Final Office Action, issued by the USPTO for corresponding U.S. Continuation-in-Part U.S. Appl. No. 14/735,276 dated Jul. 26, 2017.
Canadian Office Action, Jan. 29, 2018.
Inan, Mehmet, et al.; "The Effect of Ethanol and Acetate on Protein Expression in Pichia Pastoris," Papers in Biochemical Engineering, 2001, 15, htt[://digitalcommons.unl.edu/chemengbiochemeng/15.
"Biodiesel Handling and Use Guide." National Renewable Energy Laboratory, 4th Edition, 2009.
European Office Action; European Patent Application No. 12750156.7 dated Sep. 9, 2020.
Canadian Office Action; Canadian Patent Application No. 2,864,889 dated May 12, 2020.
Green et al "Treatment Technologies for Phosphorus Removal from water derived from Cattle Feedyards" (Year:2003).
Cicek, N. "A review of membrane bioreactors and their potential application in the treatment of agricultural wastewater," Canadian Biosystem Engineering, 2003, vol. 45. pp. 637-649.
Maurer, M. et al. "Nitrogen recovery and reuse," Water recycling and resource recoveryin industry: analysis, technologies and implentation, London 2002.
Office Action, U.S. Appl. No. 15/982,055 dated Jul. 12, 2019.
Canadian Office Action, Aug. 10, 2018, Canadian Patent Application No. 2864889.
Final Rejection; U.S. Appl. No. 15/982,055 dated Nov. 19, 2019.
Green, C. et al.; "Water Conservation Policy Alternatives for the Ogallala Aquifer in Texas," College of Agricultural Sciences and Natural Resources Report T-1-589, Aug. 2005; Can Not Locate Reference.
Canadian Office Action; Mar. 11, 2021.

* cited by examiner

SYSTEMS FOR ISOLATION AND/OR SEPARATION OF PRODUCTS FROM PRODUCTION PROCESSES

CROSS-REFERENCE TO RELATED APPLICATIONS

This application is a divisional application of co-pending U.S. patent application Ser. No. 17/089,893, filed on Nov. 5, 2020, now U.S. Pat. No. 11,839,856, which is a divisional application of U.S. patent application Ser. No. 15/922,360, filed on Mar. 15, 2018, now U.S. Pat. No. 10,894,232, which is a divisional of U.S. patent application Ser. No. 14/867,084, filed on Sep. 28, 2015, now U.S. Pat. No. 9,937,469, which is a continuation of U.S. patent application Ser. No. 13/985,367, filed on Oct. 30, 2013, now U.S. Pat. No. 9,163,265, which in turn claims priority to PCT Application No. PCT/US2012/025874 filed on Feb. 21, 2012 which in turn claims priority to U.S. Provisional Application No. 61/445,010 filed on Feb. 21, 2011, the contents of all of which are incorporated by reference herein for all purposes.

BACKGROUND OF THE INVENTION

Field of Invention

The present invention relates to separation of desired target products from numerous hydrocarbon containing materials, including biological products produced by cells, insects and/or microorganism in a culture medium; and fuels, such as ethanol, biobutanol, propanol and biodiesel from multiple sources including biological biomass, plant biomass, waste matter including cellulose materials, etc., wherein the separation of the desired target products is conducted with a cross-flow filtration system having the ability to the separate desired target products from both viscous and non-viscous medium.

Related Art in Technical Field

Throughout the world more and more companies are looking to recover value added products from a wide variety of starting materials that include hydrocarbons, such as plants, roots, root crops, grains, flowers, animal tissue, cell cultures comprising yeast, algal, bacteria, or fungi species, milk, milk products, fruits and fruit juices. Several biofuel routes have been pursued including: gasification of biomass to biogas, pyrolysis of biomass to oils, direct liquefaction, conversion of plant oils to biodiesel and release of sugars for fermentation to ethanol. Further, companies are looking to extract value added products from solid and liquid waste streams such as mill and grain wash waters, fermentation bio-mass and manure. One such waste stream includes biomass from bio-fuel production which, during the process and after production of fuels such as diesel and alcohol, is rich in plant proteins, sugars, oils and carbohydrates. Another such waste stream is cellular biomass used for protein and essential fatty acids production from wild and/or recombinant yeast, algae, bacteria, larvae or fungi species.

The production of materials in biotechnology and renewal energy involves the isolation, separation, and/or purification of a specific target molecule that is surrounded by many other biological components. It does not matter whether the material comes from fermentation processes or yard waste, the material of interest must be collected in a reasonably pure form.

The culturing of microorganisms, insect larvae, microbial cells (fermentation) or animal and plant cells (tissue culture) are central to a multiplicity of commercially-important chemical and biochemical production processes. Microorganisms, insect larvae and living cells are employed in these processes as a result of the fact that all can economically synthesize commercially-valuable chemicals. The desired product(s) can be either purified from the liquid medium or extracted from the cells themselves.

Biofuels, such as ethanol or biobutanol have widespread application as industrial chemical, gasoline additive or straight liquid fuel. As a fuel or fuel additive, both ethanol and biobutanol dramatically reduces air emissions while improving engine performance. As a renewable fuel, they reduce national dependence on finite and largely foreign fossil fuel sources while decreasing the net accumulation of carbon dioxide in the atmosphere. Such biofuels can be produced by multiple sources including microorganisms or derived from other materials that includes components such as cellulose, hemicellulose, lignin, protein and carbohydrates such as starch and sugar. Ethanol typically has been produced from sugars derived from feedstocks high in starches and sugars, such as corn. Recently, other forms including biomass from microorganisms, trees, shrubs and grasses, corn and corn husks, animal waste including manure, as well as municipal solid waste, waste paper and yard waste have been used in the production or isolation of ethanol and biobutanol.

The basic steps of biofuel production from cellulose include hydrolysis of biomass to sugars and then subsequent fermentation of sugars to ethanol. However, there are several places in the process where there are bottlenecks for efficient production of ethanol from these less expensive cellulosic wastes. Specifically, these bottlenecks include inhibitory effect of ethanol on microorganisms (inhibition due to changes in fluidity of biological membranes) and limitations on flow rate for continuous process because of the viscosity or bulk of the liquid medium. One approach to process improvement would be using a continuous fermentation integrating an ethanol removing/recovery operation, thereby maintaining the ethanol concentration in the fermentation broth at a level which is minimally inhibitory to fermenting organisms.

Attempts to address the issue of high feedstock prices have included use of less expensive feed stocks. Cellulosic biomass (agricultural waste/residue etc.) can be used for conversion to ethanol as a less expensive feedstock alternative to corn. However, it has been found that biomass and cell cultures that include highly viscous materials are far more difficult to process, such that, even though the cell culture is five (5) times denser the yield of final product is only 50% greater because the viscosity of the material prevents the separation of the desired target molecule from the mass of cellular materials. In the case of extracts of solid phase material, such as plants and animal tissue, the problem is the same such that the viscous materials clog filters and block chromatography columns as well as not separating efficiently under normal centrifugal forces.

Although it would appear that a simple dilution of the viscous material would solve the problem, this creates at least four additional problems: 1) the cost of the diluent which can be highly expensive in the case of diluents for pharmaceutical intended for human injection, 2) disposal of the higher volume of the waste stream, i.e. the original volume plus the volume of diluent, 3) the cost of the necessary tanks and mixing equipment in order to dilute the starting material, and 4) additional purification costs for the diluted final product.

Thus, when the starting mixture is very complex, isolation of the material of interest can be especially difficult and often requires costly operations. Technologies that reduce the number of separation operations and simplify recovery procedures are in high demand in biotechnology and several other industries including water treatment, ethanol production, food and beverage, and chemicals. As such, there is a need for an improved and less costly separation system that is suitable for large-scale isolation of components of interest from a complex and/or viscous sample.

SUMMARY OF THE INVENTION

The present invention relates to the production and separation processes of a target molecule from hydrocarbon containing materials, such as, biomass, sugarcane bagasse, rice hulls, corn, corn stover, wheat straw, rice straw, sugar beet pulp, citrus pulp, citrus peels, hardwood thinnings, softwood thinnings, wood chips, sawdust, pulp mill waste, urban paper waste, grass clippings, switchgrass, hybrid poplar wood, miscanthus, fiber cane, fiber sorghum, animal manure, etc.

In one aspect, the present invention provides for a separation method of at least one target molecule from hydrocarbon containing material, the method comprising the steps of:
  providing a liquid medium in a vessel wherein the liquid source medium comprises the at least one target molecule, wherein the target molecule is selected from the group consisting of ethanol, biobutanol, proteins, enzymes, sugars, starches, short or long chain fatty acids, energy containing hydrocarbons and serum components;
  providing at least one cross-flow filtration cassette comprising:
    an array of sheet members of generally rectangular and generally planar shape with main top and bottom surfaces, wherein the sheet members include in sequence in said array a first retentate sheet, a first filter sheet, a permeate sheet, a second filter sheet, and a second retentate sheet, wherein the liquid medium to be filtered flows across the filter sheets, solids or high-molecular-weight species of diameter larger than the filter sheet's pore size, are retained in the retentate flow, and at least a portion of the liquid medium with any permeate species diffuse through the filter sheets and enter the permeate sheet and permeate flow; wherein each of the sheet members in said array has at least one inlet basin opening at one end thereof, and at least one outlet basin opening at an opposite end thereof, with permeate passage openings at longitudinal side margin portions of the sheet members, wherein each of the first and second retentate sheets having a multiplicity of channel openings therein, extending longitudinally between the inlet and outlet basin openings of the sheets in the array, and being bonded to an adjacent filter sheet about peripheral end and side portions thereof, with their basin openings and permeate passage openings in register with one another and the permeate passage openings of each of the retentate sheets being circumscribingly bonded to the adjacent filter sheet, and with a central portion of each of the retentate sheets and adjacent filter sheets being unbonded to permit permeate contacting the retentate sheet to flow through the filter sheet to the permeate sheet;
  effectuating a sufficient flow of the liquid medium comprising the target molecule from the vessel through at least one cross-flow filtration cassette; and
  sequentially capturing one or more filtration fractions generated by the cross-flow filtration modules, wherein the target molecule is physically separated by said one or more cross-flow filtration and wherein said physical separation of target product is based on their different molecular weights, size and/or operating conditions.

Notably, the liquid medium comprising the target product can be pretreated to remove any unwanted material or larger solids from the liquid medium before introduction into the cross-flow filtration cassette, wherein the pretreating includes systems such as centrifuge, vibrating screen, mesh screening, belt filter, screw press, hydrocylcone and other systems that may further reduce particle size and/or remove unwanted large material to ensure easy flow through the cross-flow filtration cassette of the present invention.

Another aspect of the present invention provides for a method of separating a renewable fuel molecule from a viscous source material, the method comprising:
  contacting the viscous source material with a diluent in an amount sufficient to reduce the viscosity of the source material and form a continuous stream of diluted viscous source material, wherein the diluent is contained in a separated vessel from the viscous source material;
  flowing the diluted source material into a recirculation loop of a first cross-flow filtration cassette, wherein the cross-flow filtration cassette comprises:
    an array of sheet members of generally rectangular and generally planar shape with main top and bottom surfaces, wherein the sheet members include in sequence in said array a first retentate sheet, a first filter sheet, a permeate sheet, a second filter sheet, and a second retentate sheet, wherein each of the sheet members in said array has at least one inlet basin opening at one end thereof, and at least one outlet basin opening at an opposite end thereof, with permeate passage openings at longitudinal side margin portions of the sheet members, wherein each of the first and second retentate sheets having a multiplicity of channel openings therein, extending longitudinally between the inlet and outlet basin openings of the sheets in the array, and being bonded to an adjacent filter sheet about peripheral end and side portions thereof, with their basin openings and permeate passage openings in register with one another and the permeate passage openings of each of the retentate sheets being circumscribingly bonded to the adjacent filter sheet, and with a central portion of each of the retentate sheets and adjacent filter sheets being unbonded to permit permeate contacting the retentate sheet to flow through the filter sheet to the permeate sheet;
  diafiltering the diluted source material with sufficient diafiltration buffer so as to recover the desired yield of the renewable fuel molecule by passing the renewable fuel molecule into the first permeate fluid;
  flowing the first permeate fluid containing the renewable fuel molecule to a end product vessel;
  flowing out the first retentate solution from the recirculating liquid of the first cross-flow filtration cassette into a second cross-flow filter unit, wherein the flow rate of the first retentate solution is at the same flow rate as the diluted source material being fed into the recirculation loop of the first cross-flow filter apparatus;

diafiltering the flow of retentate into the second cross-flow filter unit with sufficient diafiltration buffer so as to recover the desired yield of the renewable fuel molecule by passing the renewable fuel molecule into the second permeate fluid;

flowing the second permeate fluid containing the renewable fuel molecule to the end product vessel;

concentrating the first and second retentate fluid by flowing same to a third cross-flow filter apparatus communicatively connected with the second cross-flow filter unit, wherein the volume of the third retentate fluid is reduced to the approximate volume of the undiluted source material or less thereby forming a waste stream for further use;

recirculating the third permeate fluid back to the diluent vessel for reuse; concentrating the first and second permeate fluid by flowing same to a fourth cross-flow filter apparatus communicatively connected to the end product vessel wherein renewable fuel molecule is concentrated and diafiltration buffer is removed in fourth permeate stream and recirculated for reuse.

In some embodiments, the source material may have a viscosity from about 100 cP to about 100,000 cP and in some instances from about 10,000 cP to about 50,000 cP and the target molecule can still be effectively separated.

In yet another aspect, the present invention provides for a method of separating and recovering target molecules from biomass, wherein the biomass includes fermentation microorganism selected from fungi, bacteria, yeast, mold, microalgae, and macroalgae, the method comprising:

providing biomass from a fermentation, culture or waste stream and optionally diluting with a diluent to reduce viscosity of the biomass:

providing at least one cross-flow filtration cassette comprising:

an array of sheet members of generally rectangular and generally planar shape with main top and bottom surfaces, wherein the sheet members include in sequence in said array a first retentate sheet, a first filter sheet, a permeate sheet, a second filter sheet, and a second retentate sheet, wherein the liquid medium to be filtered flows across the filter sheets, solids or high-molecular-weight species of diameter larger than the filter sheet's pore size, are retained in the retentate flow, and at least a portion of the liquid medium with any permeate species diffuse through the filter sheets and enter the permeate sheet and permeate flow; wherein each of the sheet members in said array has at least one inlet basin opening at one end thereof, and at least one outlet basin opening at an opposite end thereof, with permeate passage openings at longitudinal side margin portions of the sheet members, wherein each of the first and second retentate sheets having a multiplicity of channel openings therein, extending longitudinally between the inlet and outlet basin openings of the sheets in the array, and being bonded to an adjacent filter sheet about peripheral end and side portions thereof, with their basin openings and permeate passage openings in register with one another and the permeate passage openings of each of the retentate sheets being circumscribingly bonded to the adjacent filter sheet, and with a central portion of each of the retentate sheets and adjacent filter sheets being unbonded to permit permeate contacting the retentate sheet to flow through the filter sheet to the permeate sheet;

effectuating a sufficient flow of liquid comprising the biomass and target molecules from the waste stream through the at least one cross-flow filtration cassette, using one or more fluid delivery means, such as pump, wherein each fluid delivery means is connected to at least one cross-flow filtration module; and sequentially capturing one or more filtration fractions generated by the cross-flow filtration cassettes, wherein the target product is physically separated by said one or more cross-flow filtration cassette and wherein said physical separation of target product by the at least one cross-flow filtration cassette is based on their different molecular weights and/or operating conditions.

The biomass may include cellulosic material selected from the group consisting of sugarcane bagasse, rice hulls, corn stover, wheat straw, rice straw, sugar beet pulp, citrus pulp, citrus peels, hardwood thinnings, softwood thinnings, wood chips, sawdust, pulp mill waste, urban paper waste, grass clippings, switchgrass, hybrid poplar wood, miscanthus, fiber cane, fiber sorghum, animal manure and similar cellulose containing materials.

In a further aspect, the present invention provides for a method of producing renewable diesel fuel, comprising:

culturing a population of a microorganism selected from a microalgae, an oleaginous yeast or a fungus, in the presence of a fixed carbon source, wherein: (i) the microorganisms accumulate at least 10% of their dry cell weight as lipid; and (ii) the fixed carbon source is selected from the group consisting of glycerol, depolymerized cellulosic material, sucrose, molasses, glucose, arabinose, galactose, xylose, fructose, arabinose, mannose, acetate, and any combination of the foregoing;

isolating lipid components from the cultured microorganisms by using a cross-flow filtration cassette, comprising an array of sheet members of generally rectangular and generally planar shape with main top and bottom surfaces, wherein the sheet members include in sequence in said array a first retentate sheet, a first filter sheet, a permeate sheet, a second filter sheet, and a second retentate sheet, wherein the liquid medium to be filtered flows across the filter sheets, solids or high-molecular-weight species of diameter larger than the filter sheet's pore size, are retained in the retentate flow, and the at least a portion of the liquid medium with any permeate species diffuse through the filter sheets and enter the permeate sheet and permeate flow; wherein each of the sheet members in said array has at least one inlet basin opening at one end thereof, and at least one outlet basin opening at an opposite end thereof, with permeate passage openings at longitudinal side margin portions of the sheet members, wherein each of the first and second retentate sheets having a multiplicity of channel openings therein, extending longitudinally between the inlet and outlet basin openings of the sheets in the array, and being bonded to an adjacent filter sheet about peripheral end and side portions thereof, with their basin openings and permeate passage openings in register with one another and the permeate passage openings of each of the retentate sheets being circumscribingly bonded to the adjacent filter sheet, and with a central portion of each of the retentate sheets and adjacent filter sheets being unbonded to permit permeate contacting the retentate sheet to flow through the filter sheet to the permeate sheet;

subjecting the isolated lipid components to one or more chemical reactions to generate straight chain alkanes, whereby renewable diesel is produced.

In another aspect, the present invention provides for a method of producing a renewable fuel molecule from corn, the method comprising:

providing corn and introducing same into a particle reduction system to provide a mixture of corn particles with essentially the same size particles;

introducing the corn particles to liquification tank, under heat, to break apart the starch granules;

introducing enzymes for break down of the starch granules into simple sugars; introducing the simple sugars into a reaction vessel along with yeast or enzymes for conversion of the simple sugar to ethanol in a reaction medium;

moving the reaction medium into a distillation column for extraction of the ethanol from the reaction medium; and moving the remaining reaction medium with residual water and corn solids through a cross-flow filtration cassette of the present invention, wherein a significant amount of water is removed and the remaining syrup can be used as a component of animal feed.

In yet another aspect the present invention provides a method for separating components from corn, the method comprising:

providing corn particles, wherein the corn particles are separated from cobs and foreign material;

introducing the corn particles to an acidic medium, under heat, thereby releasing starch from the corn particles;

separating the released starch from the corn particles and acidic medium by moving the corn particles and acidic medium through a cross-flow filtration cassette of the present invention thereby forming a permeate comprising the released starch and a retentate comprising the corn particles; and combining the released starch with at least one saccharifying enzyme for conversion into sugars.

Sugars may include a mixture of hexose and pentose sugars, such as, glucose, xylose, arabinose, maltose and galactose.

The saccharifying enzymes may include α-amylase that can hydrolyze starch, glycogen and α-1,4 glucosidic linkages in its degradated material, to rapidly reduce the viscosity of colloidal starch solution, produce soluble dextrin and oligosaccharide, and even small amount of glucose and maltose. Glucoamylase (α-1,4-Glucanglucohydrolase), can hydrolyze α-1,4 glucosidic linkages to produce glucose from the nonreductive end, and can slowly hydrolyze α-1,6 glucosidic linkages into glucose. Other applicable enzymes may include pullulanase and β-amylase.

Additionally, if the starting material is heavily weighted toward cellulose or hemicellulose then additional or different saccharifying enzymes may be necessary for conversions to desired sugars such as for cellulose into glucose, the enzymes may include endoglucanase or EG; cellobiohydrolases (CBHs), such as (i) CBHI and (ii) CBHII; and Beta-glucosidase or BG. For hemicellulose, Beta-xylosidase and Beta 1,4-beta-xylanase may be used for conversion to xylose.

In another embodiment, the remaining corn particles in the acidic medium can be treated for separation of targets products such as releasing the whole germ from the corn particles before the degerminated corn particles proceed to the saccharification process. Specifically, the separation method comprises:

grinding the corn particles to release the whole germ from the corn kernel;

isolating the whole germ from the corn particles; and extracting corn oil from the isolated whole germ.

In still another aspect, the present invention provides for a method of producing a renewable biofuel molecule, the method comprising:

providing a bioreactor system comprising a fermentation tank and separation filtration cassette communicatively connected to the fermentation tank, wherein the fermentation tank holds biomass and any produced renewable fuel molecule, wherein the separation filtration cassette comprises a multiplicity of filter sheets in an operative stacked arrangement, wherein the filter sheets alternate with permeate and retentate sheets, wherein a liquid to be filtered flows across the filter sheets and solids or high-molecular-weight species of diameter larger than the filter sheet's pore size, are retained in the retentate flow, and the liquid along with any permeate species diffuse through the filter sheets and enter the permeate sheet and permeate flow; at least one permeate collection vessel, a retentate inlet and a retentate outlet in fluid communication with at least a first and second retentate sheet, where in the retentate sheets comprise multiple fluid-flow sub-channels each extending between the feed inlet and retentate outlet that are of equal length to one another as measured between the inlet and the outlet;

introducing the biomass to the fermentation tank and culturing the biomass in a fermentation step conducted under conditions to produce the renewable biofuel molecule;

flowing at least the fermentation liquid medium and renewable biofuel molecule from the fermentation tank to the separation filtration cassette; and capturing the renewable biofuel molecule generated by the separation filtration cassette.

Yet another aspect of the present invention relates to a method of continuously fermenting and separating a desired renewable fuel including a biomass and reactive microorganisms to convert the biomass into a renewable fuel comprising the steps of:

providing at least a first reactor vessel wherein the reactor vessel comprises the biomass and reactive microorganisms useful in converting the biomass into a renewable fuel;

locating a cross-flow filtration system downstream from the first reactor vessel and configured to receive at least a portion of the biomass to separate into at least a first retentate and a first permeate, wherein the reactive microorganisms are generally retained in the retentate by the cross-flow filtration cassette and returned to the first reactor vessel; and isolating the renewable fuel from the permeate.

In a further aspect, the present invention provides for a system for converting cellulose and/or sugar containing source material such as garden waste, farm waste, plant waste to energy containing molecules, the system comprising:

at least one colloid or hammer mill for reducing the particle size of cellulose and/or sugar containing source material to produce an emulsified or homogenized source material;

at least one fermentation unit in fluid communication with the colloid or hammer mill for accepting the emulsified or homogenized source material;

at least one cross-flow filtration cassette in fluid communication with the fermentation unit for separating the energy containing molecules from the source material, wherein the cross-flow filtration cassette comprises a multiplicity of filter sheets in an operative stacked arrangement, wherein the filter sheets alternate with permeate and retentate sheets, wherein a liquid to be filtered flows across the filter sheets and solids or high-molecular-weight species of diameter larger than the filter sheet's pore size, are retained in the retentate flow, and the liquid along with any permeate species diffuse through the filter sheets and enter the permeate sheet and permeate flow; at least one permeate collection vessel, a retentate inlet and a retentate outlet in fluid communication with at least a first and second retentate sheet, where in the retentate sheets comprise multiple fluid-flow sub-channels each extending between the feed inlet and retentate outlet that are of equal length to one another as measured between the inlet and the outlet; and at least one collection vessel in fluid communication with the cross-flow filtration cassette for holding the separated energy containing molecules.

Yet another aspect of the present invention provides for a method for increasing concentration of thin stillage removed from an ethanol production system, the method comprising:

moving the thin stillage through a cross-flow filtration cassette of the present invention to provide a liquid containing at least 30% solids and wherein water removed from the stillage is reused in the ethanol production system.

In a still further aspect, the present invention provides for separation of products and chemicals involved in a chemical pretreatment of cellulose biomass. Chemical pretreatment is important in the overall conversion scheme from the choice of biomass to the size reduction, hydrolysis, fermentation and the recovery of biofuel product and other co-products. Chemical pretreatment includes using any of dilute acid, sulfur dioxide, ammonia and lime $(Ca(OH)_2)$. However, using these chemical pretreatments may provide a fermentable product but the choice of chemical should not present processing or disposal challenge of any formed products. Lime is used for pretreatment because it removes lignin and acetyl groups that have been known to affect hydrolysis rates. However, use of lime produces waste products such as gypsum which is generated during the pH adjustment and conditioning of hydrolyzates from pretreatment prior to enzymatic hydrolysis and fermentation. Thus, the separation of any generated gypsum is necessary and can be easily removed by use of the systems of the present invention by placing a cross-flow filtration cassette between the pretreatment vessel and that of the container used for enzymatic hydrolysis. The gypsum containing media is often very viscous, however, using the cross-flow filtration cassette of the present invention retains the gypsum while allowing the sugar pass through the membrane.

Another aspect provides for preparation of polymers obtained from agro-resources such as polysaccharides to replace conventional plastic materials. To obtain a thermoplastic material, cellulose, lignins, lignin-cellulose and other starch containing material are used in the process. Separation of microfibrils materials from the polysaccharide containing material provides for polymeric type material for further conversion to polymers. The present invention provides for separation with the cross-flow filtration cassettes, to isolate the monocrystals for further development of the polymeric material.

Other aspects and advantages of the invention will be more fully apparent from the ensuing disclosure and appended claims.

DETAILED DESCRIPTION OF THE INVENTION

Figure 1:
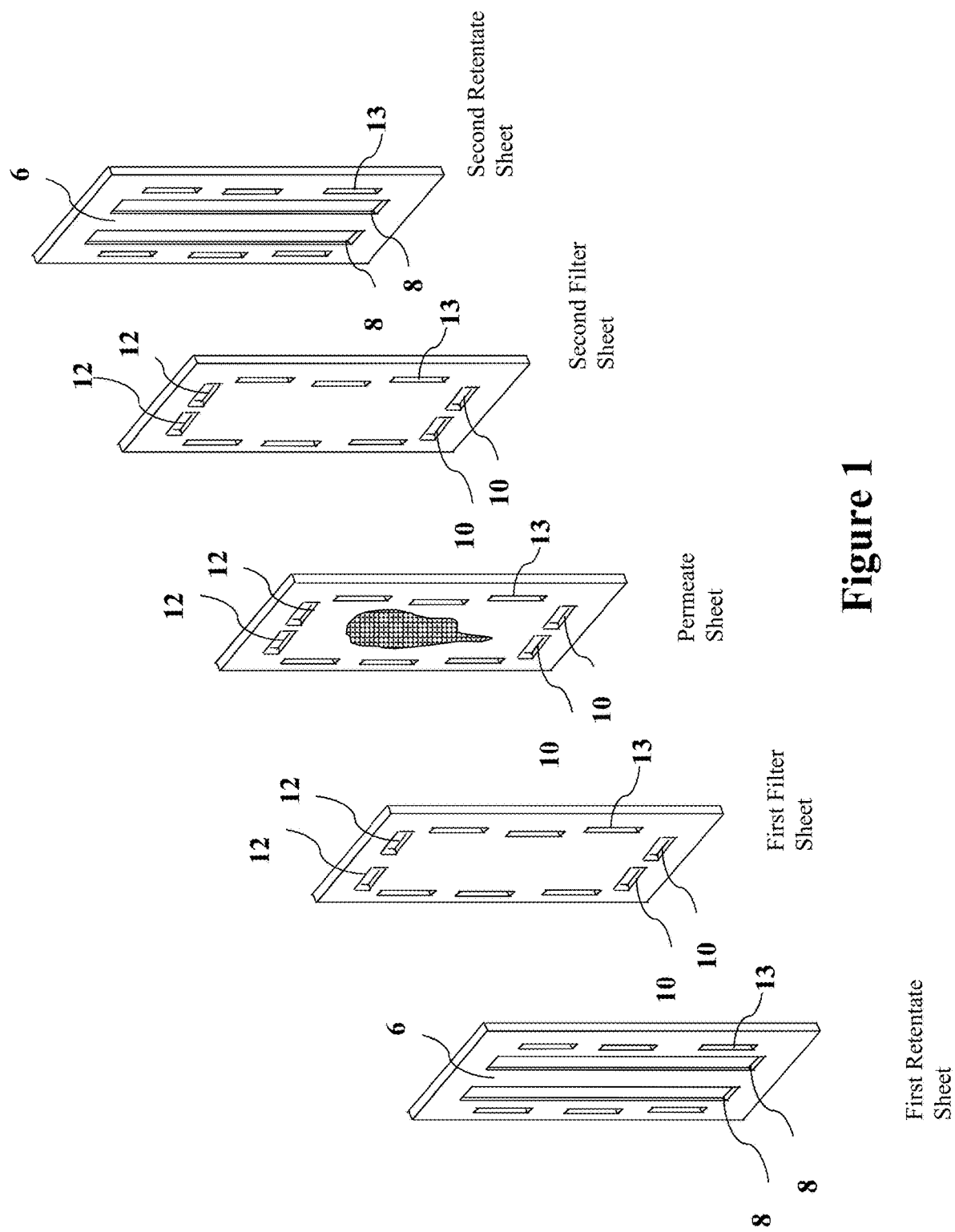
FIG. 1 shows the components of a cross-flow filtration cassette used in the separation of renewable fuels

While not to be construed as limiting, the terms used herein have the following definitions unless indicated otherwise.

The term "biomass" refers to any material that includes cellulosic or lignocellulosic materials; cellulose, hemicellulose, lignin, starch, proteins, lipids, oligosaccharides, polysaccharide and/or monosaccharides. According to the present method, biomass may be derived from a single source, or biomass can comprise a mixture derived from more than one source; for example, biomass could comprise a mixture of corn cobs and corn stover, or a mixture of grass and leaves. Biomass may include, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from processing of grains, trees, branches, roots, leaves, wood chips, sawdust, shrubs and bushes, vegetables, fruits, flowers, animal manure and municipal waste.

The term "byproducts" refers to any and all materials produced during or remaining after the separation of the desired target molecule from the hydrocarbon containing material.

The term "conversion" refers to any biological, chemical and/or bio-chemical activity which produces biofuels and byproducts from the hydrocarbon containing material, such as biomass or blended biomass. Such conversion may include any one of the following processes including hydrolysis, fermentation, and simultaneous saccharification and fermentation (SSF) processes.

The term "deleterious materials" refers to any organic or inorganic material which has the ability to degrade or limit fermentation materials or hydrolysis materials in any manner, including the prevention or retardation of the hydrolysis conversion of any biomass or its fermentation to biofuels. Examples of deleterious materials include ferrous metals, non-ferrous and heavy metals, grit, dirt, dyes, plastics, clays, gypsum, solvents, pesticides, herbicides, preservatives, paints, stains, glues, adhesives, and certain phenolic compounds and resins, for example those present in soft wood.

The term "ethanol" refers to ethyl alcohol or mixtures of ethyl alcohol and water.

The term "cross-flow filtration cassette" refers to a type of filter module or filter cassette that comprises a porous filter element across a surface of which the liquid medium to be filtered is flowed in a tangential flow fashion, for permeation through the filter element of selected component(s) of the liquid medium. In a cross-flow filter, the shear force exerted on the filter element (separation membrane surface) by the flow of the liquid medium serves to oppose accumulation of solids on the surface of the filter element. Cross-flow filters include microfiltration, ultrafiltration, and nanofiltration systems. The cross-flow filter may comprise a multiplicity of filter sheets (filtration membranes) in an operative stacked arrangement, e.g., wherein filter sheets alternate with permeate and retentate sheets, and as a liquid to be filtered flows across the filter sheets, impermeate species, e.g. solids or high-molecular-weight species of diameter larger than the filter sheet's pore size, are retained and enter the retentate flow, and the liquid along with any permeate species diffuse through the filter sheet and enter the permeate flow. In the practice of the present invention, cross-flow filtration is a preferred separation method. Cross-flow filter modules and cross-flow filter cassettes useful for such filtration are commercially available from Smartflow Technologies, Inc. (Apex, N.C.). Suitable cross-flow filter modules and cassettes of such types are variously described in the following United States patents: U.S. Pat. Nos. 4,867,876; 4,882,050; 5,034,124; 5,034,124; 5,049,268; 5,232,589; 5,342,517; 5,593,580; and 5,868,930; the disclosures of all of which are hereby incorporated herein by reference in their respective entireties.

The term "fermentation microorganisms" refers to any organism capable of producing biofuels, such as ethanol, biobutanol or lipids, such as fatty acids, for conversion to diesel. Preferred fermenting organisms for use in the present invention are ethanol-producing bacteria, yeast, algae, fungi strains or derivatives thereof. While not to be construed as limiting, the term encompasses bacteria, such as *Zymomonas mobilis* and *Escherichia coli*; yeasts such as *Saccharomyces cerevisiae* or *Pichia stipitis*; and fungi that are natural ethanol-producers including a species from the genus *Mortierella, Mortierella vinacea, Mortierella alpine, Pythium debaryanum, Mucor circinelloides, Aspergillus ochraceus, Aspergillus terreus, Penicillium lilacinum*; a species of the genus *Hensenula*, a species of the genus *Chaetomium*, a species of the genus *Cladosporium*, a species of the genus *Malbranchea*, a species of the genus *Rhizopus*, and a species of the genus *Pythium*. Fermentation microorganisms may also encompass engineered organisms that are induced to produce ethanol or enzymes through the introduction of foreign genetic material (such as pyruvate decarboxylase and/or alcohol dehydrogenase genes from a natural ethanol producer; exogenous sucrose utilization gene, such as a sucrose transporter, a sucrose invertase, a hexokinase, a glucokinase, or a fructokinase; a lipid pathway enzyme, such as a stearoyl-ACP desaturase, a glycerolipid desaturase, a pyruvate dehydrogenase, an acetyl-CoA carboxylase, an acyl carrier protein, and a glycerol-3 phosphate acyltransferase.). The term further encompasses mutants and derivatives, such as those produced by known genetic and/or recombinant techniques, of ethanol-producing organisms, which mutants and derivatives have been produced and/or selected on the basis of enhanced and/or altered ethanol production. Bacterial strains may include thermophilic bacteria including phototrophic bacteria (i.e., the purple bacteria, green bacteria, and cyanobacteria), bacteria (i.e., *Bacillus, Clostridium, Thiobacillus, Desulfotomaculum, Thermus*, Lactic acid bacteria, Actinomycetes, Spirochetes, and numerous other genera). Many hyperthermophiles are archaea (i.e., *Pyrococcus, Thermococcus, Thermotoga, Sulfolobus*, and some methanogens). There are aerobic as well as anaerobic thermophilic organisms. Thus, the environments in which thermophiles may be isolated vary greatly, although all of these organisms are isolated from areas associated with high temperatures.

The term "an oleaginous yeast" refers to a selected microbe from the group consisting of *Cryptococcus curvatus, Cryptococcus terricolus, Candida* sp., *Lipomyces starkeyi, Lipomyces lipofer, Endomycopsis vernalis, Rhodotorula glutinis, Rhodotorula gracilis*, and *Yarrowia lipolytica*.

The term "fermentable sugar" refers to oligosaccharides and monosaccharides that can be used as a carbon source by a microorganism in a fermentation process.

The term "lignocellulosic" refers to a composition comprising both lignin and cellulose. Lignocellulosic material may also comprise hemicellulose.

The term "saccharification" refers to the production of simple sugars from complex carbohydrates.

The terms "suitable conditions to produce fermentable sugars" refers to conditions such as pH, composition of medium, and temperature under which saccharification enzymes are active.

The term "hydrolysis materials" refers to any material suitable for the hydrolysis of cellulose and hemicellulose to any hexose and pentose sugar, including dilute and concentrated sulfuric acid and enzymes such as those excreted by *Trichoderma reesei*.

The term "municipal solid waste" refers to garbage, trash, rubbish and refuse that are normally disposed of by the occupants of residential dwelling units and by business, industrial and commercial establishments, including but not limited to: paper and cardboard, plastics, food scraps, ferrous and non-ferrous metals, wood, lumber, glass, leather, grit or dirt.

The term "homogenizer," "colloid mill" or hammer mill refers to a machine that is used to reduce the particle size of a solid in suspension in a liquid, or to reduce the droplet size of a liquid suspended in another liquid. Preferably, this can be accomplished by applying high levels of hydraulic shear to the process and the machine provides a finished product that is homogeneous, has repeatable viscosity and dispersion down to one micron, and is totally consistent from batch-to-batch. Preferably, the colloid mill further includes a positive displacement feed pump and can handle viscous materials from 1,000 CPS and up with flow rates from 0.5 up to 300 GPM.

The term "biobutanol" refers to a four carbon alcohol derived from the fermentation of biomass including simple sugars. Biobutanol has a higher energy content that ethanol, of about 105,000 BTO/gallon versus ethanol of 84,000/BTU/gallon. Biobutanol can also be used as industrial solvent, degreasers, paint solvent, etc. The additional of biobutanol to an engine does not require special adaptation of the engine and can be combined with gasoline at a rate of 16% which is higher than ethanol.

In one particular aspect, the present invention relates to a cross-flow filtration cassette, as shown in FIG. 1, comprising a multilaminate array of sheet members of generally rectangular and generally planar shape with main top and bottom surfaces, wherein the sheet members include in sequence in said array a first retentate sheet, a first filter sheet, a permeate sheet, a second filter sheet, and a second retentate sheet, wherein each of the permeate and filter sheet members in said array has at least one inlet basin opening 10 at one end thereof, and at least one outlet basin opening 12 at an opposite end thereof, with permeate passage openings 13 at longitudinal side margin portions of the sheet members; each of the first and second retentate sheets having at least one channel opening 8 therein, extending longitudinally between the inlet 10 and outlet basin 12 openings of the permeate and filter sheets in the array, and being compression bonded to an adjacent filter sheet about peripheral end and side portions thereof, with their basin openings and permeate passage openings in register with one another and the permeate passage openings of each of the retentate sheets being circumscribingly compression bonded to the adjacent filter sheet, and with a central portion of each of the retentate sheets and adjacent filter sheets being unbonded to permit permeate contacting the retentate sheet to flow through the filter sheet to the permeate sheet; and each of the filter sheets being secured at its peripheral portions on a face thereof opposite the retentate sheet, to the permeate sheet.

The term "sheet" will denote the generally planar members of the cassette, the cassette thus comprising an assembly of permeate sheets, filter sheets, and retentate sheets, coupled to one another in such manner as to permit flow of the fluid to be separated through the flow channel(s) of the device, for mass transfer involving passage of the permeate through the filter sheets, and retention of the retentate on the side of the filter sheet opposite the side from which the permeate emerges.

The term "compressible" in reference to the retentate sheet or other structural feature or sheet member of the present invention means that such component or member is compressively deformable by application of load or pressure thereon.

The above-described filtration cassette of the invention comprises a "base sequence" of elements, defined as a sequence of sheet elements constituting a compressible retentate sheet (hereafter designated by the symbol "CR"), a filter sheet (hereafter designated by the symbol "F"), a foraminous permeate sheet (hereafter designated by the symbol "P"), a second filter sheet ("F"), and a second compressible retentate sheet ("CR"), thereby providing a sequence of sheet elements, CR/F/P/F/CR.

Figure 2:
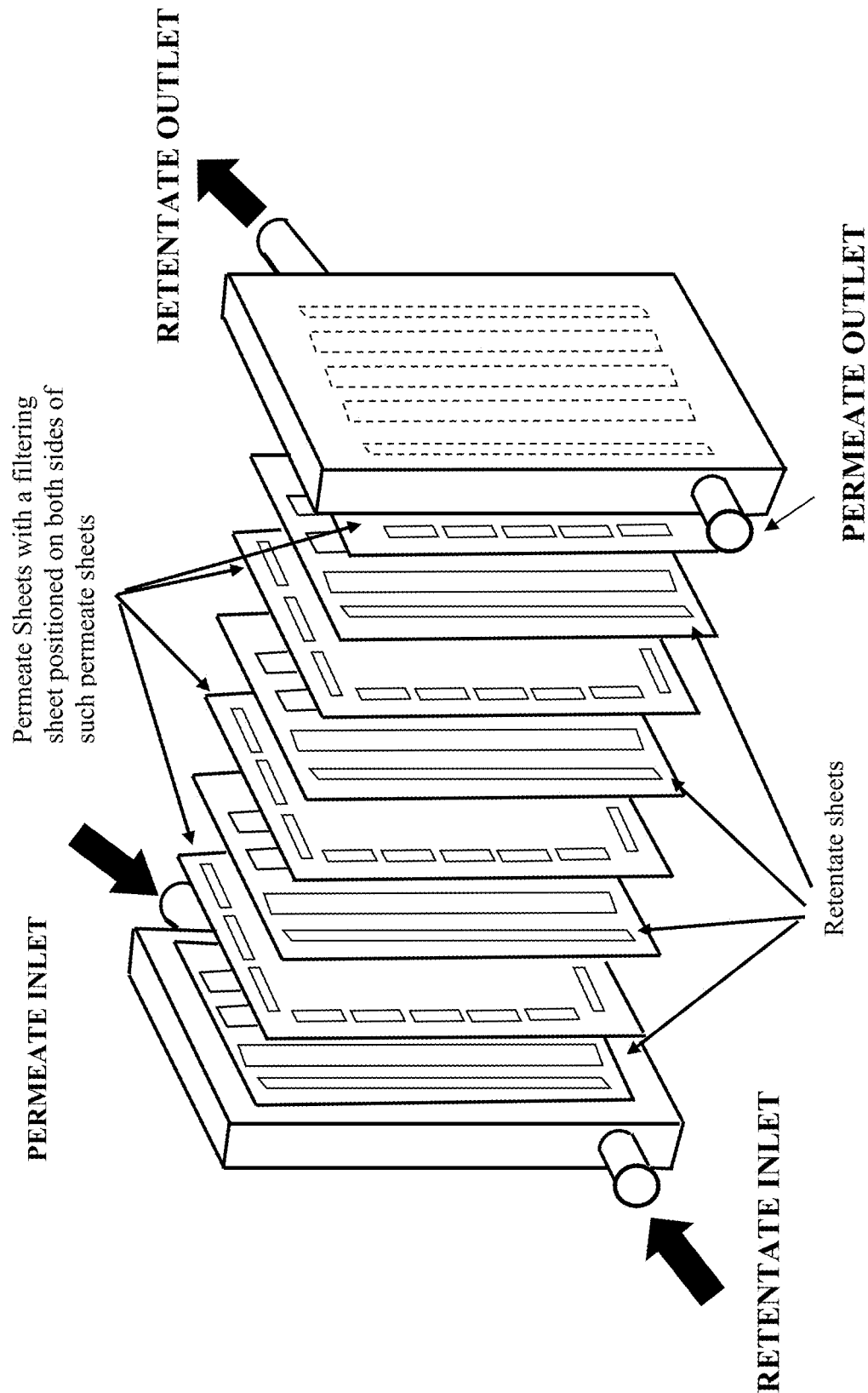
FIG. 2 shows the flow pattern of the retentate through a multiplicity of sheets adapted to end plates with retentate inlet and outlet and permeate inlet and outlet.

The base sequence of sheet elements may be utilized in construction of filters comprising a plurality of filtration cassettes, wherein the compressible retentate sheet is utilized to seal the top and bottom elements of a plurality of filtration cassettes of a sequence, comprising compressible retentate sheet "CR", filter sheet "F", foraminous permeate sheet P, filter sheet "F", non-compressible retentate sheet "R", filter sheet "F", foraminous permeate sheet P, filter sheet "F", and compressible retentate sheet "CR". An illustrative stacked cassette filter according to the invention may for example feature the sheet sequence CR/F/P/F/R/F/P/F/R/F/P/F/CR as shown in FIG. 2, comprising a first compressible retentate sheet, two base sequences of sheets FPFRFPF in a repetitive sequence, and a second compressible retentate sheet. In all repetitive sequences, other than a single cassette base sequence, the following relationship is observed: where X is the number of filter sheets F, the quantity $0.5X - 1$ is the number of non-compressible retentate sheets R, and the quantity $0.5X$ is the number of foraminous permeate sheets P, with two compressible retentate sheets being utilized to seal the top and bottom extremities of the intervening sequence.

Thus, it is possible to utilize a large number of base sequence cassettes in a repetitive sequence, to provide a stacked cassette filter of the desired mass transfer area. Many configurations are possible. It is feasible in some instances, e.g., for mass transfer studies and system quantitation, to utilize a single cassette comprising the base sequence CR/F/P/F/CR wherein the outermost retentate sheets in the sequence are compression-sealed at their outer faces to an end plate accommodating removal of permeate from the permeate passage openings of the constituent sheet members in the cassette.

The sheets of filter material used in the cassette article of the present invention may be of any suitable porosity rating. As used herein, the porosity rating of a sheet of filter material is the smallest particle size which cannot pass through the pores of the filter material. Typical porosity ratings are expressed in molecular weight (MW) and micrometer units, e.g., a 2 micron filter media sheet being a material which will pass particles smaller than 2 microns in diameter through the pores of the material, while particles larger than 2 microns will not be passed through the filter material, and as a further example, a 10,000 MW filter media sheet being a material which will pass particles smaller than 10,000 MW in diameter through the pores of the material, while particles larger than 10,000 MW will not be passed through the filter material.

In one preferred embodiment of the cassette article of the present invention, a retentate sheet is provided with a plurality of transversely spaced-apart, longitudinally extending ribs or partitions, extending upwardly from (the central portion of) each of the main top and bottom faces of the retentate sheet, such ribs or partitions being of substantially the same height and substantially parallel to one another to define a series of channels between the partitions, extending longitudinally between the respective basin openings of the retentate sheet, on both faces thereof. The adjacent filter sheets may be further bonded to the outer extremities of the ribs or partitions, and the ribs or partitions may be formed of any suitable material, e.g., a flexible resilient adhesive bonding medium, such as a urethanes, epoxy or silicone adhesive sealant medium, e.g., applied in a "bead" in the longitudinal direction of the retentate sheet on both main top and bottom faces thereof.

The term "bonded" in reference to adjacent sheets in the multilaminate cassette means that the adjacent sheets are secured to one another in such manner as to prevent flow of the material being processed, e.g., the feed material to be separated, as well as component materials therefrom (filtrate or permeate, as well as retentate), from flowing through such secured areas or between the adjacent sheets at such secured areas. Preferably, the bonding is carried out by compressive bonding or with a suitable adhesive or sealant medium, e.g., a urethane, epoxy, cyanoacrylate, or silicone adhesive material, which fills the interstices of the foraminous sheet in the bonded pair of sheets, and adhesively joins one of the adjacent sheets to the other in the bonded areas.

The term "compressive bonding" and "compressively bonded" refer to bonding and bonding operations in which the structure being bonded is subjected to a compressive load or force, for sufficient time and under sufficient period to effect the bonding securement of the structure. Compressive bonding of laminae in the practice of the invention is highly desirable, in order to assure the leak-tightness and structural integrity of the resulting multilaminate assembly of the cassette.

The invention may for example be carried out with bonding of sheets in the multilaminate array to one another with cyanoacrylate or other "fast" adhesives, or alternatively the adhesive or sealant medium may require extended cure at ambient temperature or other appropriate cure conditions, and it may be advantageous to conduct such cure with the laminate structure in a fixture or other assembly in which the compressive bonding is effectively completed.

In a specific aspect of the invention, each of the foraminous permeate sheets may constitute a foraminous material of from about 80 to about 300 mesh size. Each of the foraminous permeate sheets may for example comprise a woven polymeric mesh, e.g., of a material selected from the group consisting of polyester, polypropylene, nylon, fluorocarbon polymers such as polytetrafluoroethylene, polyethylene, and polysulfone, and composites comprising one or more of such materials.

The filter sheets used in the filtration cassette of the present invention may be of any suitable materials, such as a material selected from the group consisting of cellulose, polyphenylene oxide, polysulfone, cellulose nitrate, cellulose acetate, regenerated cellulose, polyether amide, polyphenylene oxide/polysulfone blends, mixed esters of cellulose, and polyether sulfone.

Furthermore, it is possible to optimize the separate processes with cross-flow filtration modules of variable channel velocities but of uniform channel heights, given the fact that most commercial cross-flow modules are only available in a single channel height. When the channel height of a cross-flow filtration module is known, shear is directly proportional to channel velocity of such module for the same solution passing by.

In the literature, numerous techniques have been proposed to effect the separation of target substances using membrane separations with addition of foreign substances such as acid, base, salt and solvents. In contrast to these chemical additives-based methods, the methodology of the present invention permits a target substance to be separated from an input fluid by the simplest mechanical means. In the use of cross-flow filtration modules of the type described in the aforementioned patents, the specificity and speed of a desired separation is effected by a) fluid distribution in the cross-flow module, b) channel height of the cross flow module, c) channel length, d) shear rate, e) membrane pore structure, f) membrane structure, g) membrane chemistry, h) trans-membrane pressure, and i) pressure drop, which is a function of channel length, velocity and solution viscosity.

The approaches by others involving various additives and manipulations of transmembrane pressure appear to be predicated on overcoming problems created by poor distribution of flow within the cross-flow module. It is not to say that the addition of salts and solvents do not have a place in separation but without proper flow distribution the membrane separation cannot be optimally operated nor will cleaning techniques be fully beneficial. It will be appreciated, based on the disclosure herein that numerous heretofore expensive or difficult separations are rendered far simpler and more economical by employing the techniques described herein.

Thus, the invention relates in another aspect to optimizing the membrane separation process, comprising:
  selecting a cross-flow membrane module wherein the distance from the inlet port to the outlet port is equidistant from the inlet to outlet for each sub-channel of the device, i.e., each sub-channel is of a same dimensional character;
  selecting an optimal channel height;
  selecting an optimal shear rate and/or channel velocity;
  selecting an optimal transmembrane pressure;
  selecting an optimal membrane pore size;
  selecting an optimal temperature;
  selecting an optimal channel length; and
  selecting an optimal pressure drop which is the composite of
    the optimal channel height;
    the optimal shear rate and/or channel velocity;
    optimal channel length; and
    the viscosity of the solution being filtered.

Selecting a channel height can be performed mathematically or empirically by trial and error. In most cell fermentation applications, trial and error has been more appropriate due to the fact that the viscosity of the cell broth or product solution is rarely known, the cell count and cell viability are highly variable, and the solution is frequently non-Newtowian. The objective of channel selection is to minimize channel height with three critical stipulations: first, the channel must be sufficiently high to allow the unrestricted passage of any larger material such as clumped cells; second, the channel should not cause excessive pressure drop and loss of linear efficiency; and third, the channel should be sufficiently high as to allow the proper angle of attack for substances to encounter the membrane pore and pass through the pore. The optimal channel height is dependent on the length and viscosity of the solution.

Several notable observations have been made in initial trials and process scale-up, as discussed below.

For suspensions having an optical density (OD) of 2 to 500, and a path length of 6 to 12 inches, start with a channel height between 0.4 to 0.75 mm. If the inlet pressure is above 15 PSIG at a velocity of 2.0 M/sec, then the channel is too thin.

For suspensions having an optical density (OD) of 2 to 500, and a path length of 6 to 12 inches, start with a channel height between 0.4 to 0.75 mm. If the inlet pressure is below 5 PSIG at a velocity of 2.0 M/sec the channel is too high.

For suspensions having an optical density (OD) of 2 to 500, and a path length of 25 to 40 inches, start with a channel height between 0.7 to 1.0 mm. If the inlet pressure is above 15 PSIG at a velocity of 2.0 M/sec, the channel is too thin.

For suspensions having an optical density (OD) of 2 to 500, and a path length of 25 to 40 inches, start with a channel height between 0.7 to 1.0 mm. If the inlet pressure is below 5 PSIG at a velocity of 2.0 M/sec, the channel is too high.

Another aspect of the present invention relates to a stacked cassette cross-flow filter comprising cassette articles of the type described above.

Still another aspect of the present invention relates to a pair of end plates or manifold assembly in which the cassettes are secured for operation as shown in FIG. 2.

Figure 3:
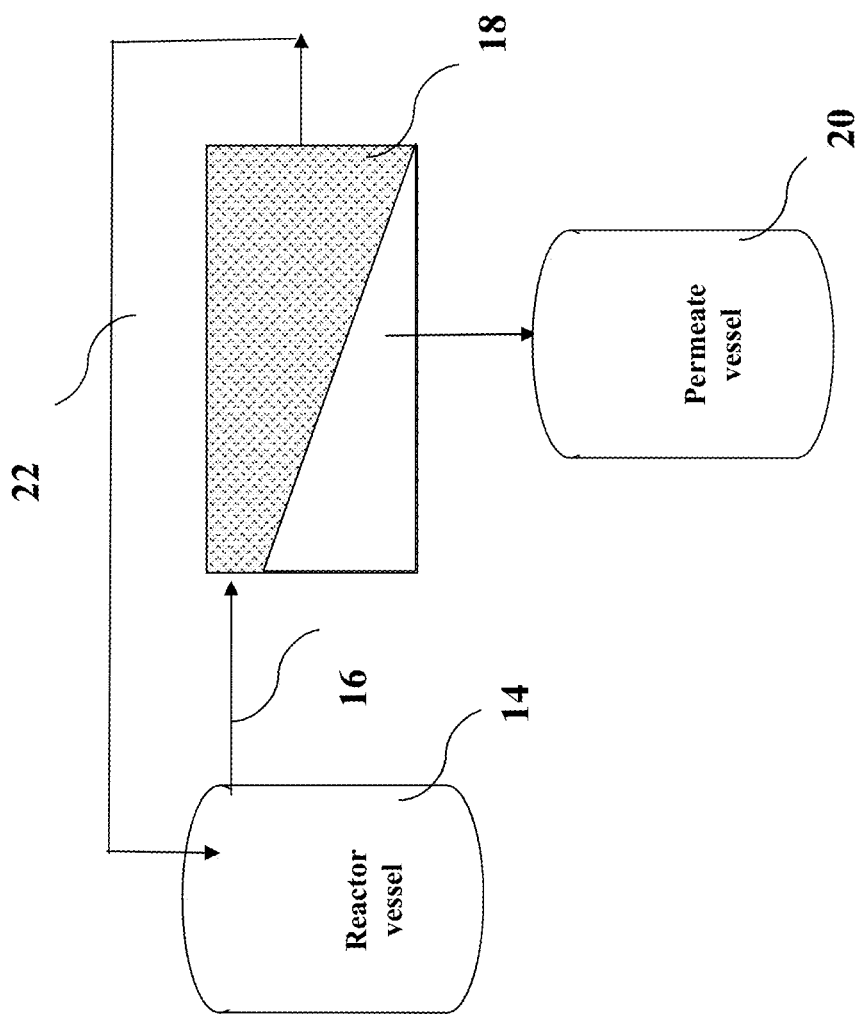
FIG. 3 shows a system for fermentation and separation of a desired target.

Referring to FIG. 3, a reactor vessel 14 is shown in which incoming biomass may be at least partially processed into a target product, such as renewal fuel and fermentation microorganisms may be recovered and returned to after separation through the cross-flow filtration cassette 18 Although FIG. 3 shows only one reactor vessel, the actual number of reactor vessels that may be incorporated into system is unlimited and reactor vessels may be added in series or in parallel, to accommodate individual needs and production goals.

Reactor vessel sizes of 200 gallons to 50,000 gallons are envisioned for advantageous use, although smaller or larger vessel sizes may be used. While it is envisioned that processing stoppage and cleaning between continuous processing runs will be required, it is currently envisioned that continuous processing runs of two weeks or more may be permissible.

In the reactor vessel 14, the biomass may be a carbohydrate agricultural product, or byproduct. In general where the target product is ethanol, the higher the carbohydrate percentage of the biomass, the greater the potential production of ethanol where other factors are constant. The biomass for use with the process invention may include a number of starch-, sugar- and cellulosic-based products and by-products. As non-limiting examples, starch-based substrates which may be used include, but are not limited to: lactose, whey, whey permeate, corn, wheat, rye, rice, potatoes, and artichokes. Sugar-based substrates which may be used include, but are not limited to: sugar beets, sugarcane, and fruits. Cellulosic-based substrates which may be used include, but are not limited to: wood by-products, wood fiber, plant fiber, paper and various grasses (e.g., prairie grass), as some examples.

Some different considerations come into play if different substrates are used. For example, if cellulosic-based biomass is used, a two-step process is necessary, as the cellulosic material will first be converted into sugar, and the sugar will then be fermented into alcohol. These two steps may occur in the same reactor vessel, or may be caused to occur in consecutive, different vessels.

Chemical stabilization of the fermentation process may be enhanced by introducing sterilizing chemicals to the biomass to exclude organisms that may compete with the desired fermentation microbe. Sterilizing chemicals may include, but are not limited to, hydrogen peroxide and sodium sulfite. The stabilizing chemicals may be introduced prior to the first reactor and/or into any or all bioreactors individually or collectively prior to, or during, the fermentation process.

In some embodiments, fermentation microorganisms may be added when the reactor vessel is 10% full with biomass. Oxygen, or gas or fluid containing oxygen, may be introduced to the reactor vessel. In one preferred embodiment, after loading the reactor vessel and during operation of the system, a portion of the content of the reactor, that being, the biomass may be continuously removed from the reactor, moved through the cross-flow filtration cassette, and portions are returned to the reactor vessel. In other embodiments, the biomass may be periodically and/or intermittently removed from the reactor vessel, moved through the cross-flow filtration cassette, and returned to the bioreactor. In some embodiments the process of removing a portion of the biomass may commence after the reactor vessel is about 75% full with biomass.

A portion of the contents of reactor vessel is removed from the reactor vessel and is introduced, via line 16, to the cross-flow filtration cassette 18 wherein the biomass is separated into a retentate and a permeate. The retentate is returned to the reactor vessel via process line 22 and the permeate is introduced to the permeate vessel 20.

The components of the cross-flow filtration cassette 18 are described in FIG. 1 and relates to the separation of a target molecule, such as a renewal fuel molecule, and the separation is facilitated by the use of a filtration cassette comprising a multilaminate array of sheet members of generally rectangular and generally planar shape with main top and bottom surfaces, wherein the sheet members include:

a first compressible retentate sheet of suitable material, e.g. polysulfone, polyethersulfone, polycarbonate, urethane, silicone, or other compressible material of construction, having (i) at least one longitudinally extending rib or partition element 6, such partition element(s) when provided in multiple configuration being transversely spaced apart from one another and being of substantially the same height and substantially parallel to one another to define a single or a series of channels 8 between the partitions, extending longitudinally between the respective inlet 10 and outlet 12 basin openings of associated filter elements and permeate sheet members, on both faces thereof, (ii) permeate passage openings 13 at side portions of the sheets, and (iii) the retentate sheet aligned to the first sheet of filter material at respective end and side portions thereof, with the basin openings and permeate passage openings of the associated sheet members in register with one another and the permeate passage opening of the retentate sheet member being circumscribingly compressed to the first sheet of filter material, and with a central portion of the first sheet of filter material and the retentate sheet member being unbonded to permit permeate contacting the retentate sheet member to flow through the first sheet member of filter material to the foraminous permeate sheet member;

a first sheet member of filter material having (i) multiple basin openings, of a suitable shape, e.g., polygonal, semicircular, or sector shape, at each of opposite end portions of the sheet member defining respective inlet 10 and outlet 12 passages, each basin being bounded by generally linear side edges defining corners of the basin at respective intersections of the side edges, and (ii) permeate passage openings 13 at the side portions of the sheet member, wherein the first sheet member of filter material is bonded to the foraminous permeate sheet member at their respective end and side portions, with their basin openings and permeate passage openings in register with one another and the basin openings being circumscribingly bonded at respective end portions of the first sheet member of filter material and the foraminous permeate sheet member, and with a central portion of the first sheet member of filter material and the foraminous permeate sheet member being unbonded so as to define a central portion permeate channel of the foraminous permeate sheet communicating with the permeate passages in the first sheet member of filter material and in the foraminous permeate sheet member;

a forminous permeate sheet member of screen or mesh material, having (i) multiple basin openings of suitable shape at each of opposite end portions of the sheet member defining respective inlet 10 and outlet 12 passages, each basin being bounded by generally linear side edges defining corners of the basin at respective intersections of the side edges, and (ii) permeate passage openings 13 at the side portions of the sheet member;

a second sheet member of filter material having (i) multiple basin openings at each of opposite end portions of the sheet member defining respective inlet 10 and outlet 12 passages, each basin being bounded by generally linear side edges defining corners of the basin at respective intersections of the side edges, and (ii) permeate passage openings 13 at the side portions of the sheet member, wherein the second sheet member of filter material is compression sealed to the retentate sheet member at their respective end and side portions, with their basin openings and permeate passage openings in register with one another and the permeate passage opening of the retentate sheet member being compression sealed to the second sheet member of filter material, and with a central portion of the second sheet member of filter material and the retentate sheet member being unbonded to permit permeate contacting the retentate sheet member to flow through the second sheet member of filter material; and a second compressible retentate sheet member of suitable material, e.g. polysulfone, polyethersulfone, polycarbonate, urethane, silicone, having (i) at least one longitudinally extending rib or partition element 6, provided that when multiple partition elements are employed, the partition elements are transversely spaced-apart from one another, such partition elements being of substantially the same height and substantially parallel to one another, to define a single channel 8 or a series of channels between the partitions, extending longitudinally between the respective inlet and outlet basin openings of the filter elements and permeate sheet members, on both faces thereof, (ii) permeate passage openings 13 at the side portions of the sheet member, and (iii) the retentate sheet compression sealed to the second sheet of filter material at respective end and side portions thereof, with their basin openings and permeate passage openings in register with one another and the permeate passage opening of the retentate sheet member being compression sealed to the second sheet member of filter material, and with a central portion of the first sheet member of filter material and the retentate sheet member being unbonded to permit permeate contacting the retentate sheet member to flow through the second sheet member of filter material to the foraminous permeate sheet member.

In operation, the cross-flow filtration cassette provides a barrier through which microorganisms are substantially restricted from passing through the filter sheets and allows microorganism concentration to be increased and maintained at optimal levels in the reactor vessel. This enables microorganism concentrations to be restricted for controlled, and/or optimum, rate of conversion of substrate to target product.

After passing through the cross-flow filtration cassette, the permeate preferably does not include microorganisms to an extent significant enough to hinder any further separation of the ethanol from the permeate. The first retentate, which is returned to reactor vessel may still include some of the target product (ethanol), biomass which was not previously converted into ethanol, unconverted sugars and/or starches, microorganisms including the fermentation microorganisms, and other non-substrate nutrients.

In the event the fermentation microorganism cell mass in the reactor vessel exceeds a desirable level, instead of returning all of the first retentate back to the reactor vessel, a portion of the first retentate, including the fermentation microorganism cell mass, may be bled off to a second cross-flow filtration cassette for separating the microorganisms from the other components of the retentate.

In operation, after the reactor vessel receives a fermentation microorganism, such as yeast, and a biomass and the fermentation microorganism begins processing the substrate to yield the ethanol and possible byproducts such as carbon dioxide, low molecular weight organics, and some minerals and/or salts. Oxygen and other nutrients can be added. In the case of ethanol, oxygen may be limited to allow anaerobic production of ethanol from yeast. Temperature in reactor vessel may also be controlled and monitored. In the case of ethanol production, the temperature is generally maintained at a range from about 25° C. to about 45° C. Agitation of the contents of the reactor vessel may be achieved through mechanical agitation devices known in the art.

Figure 4:
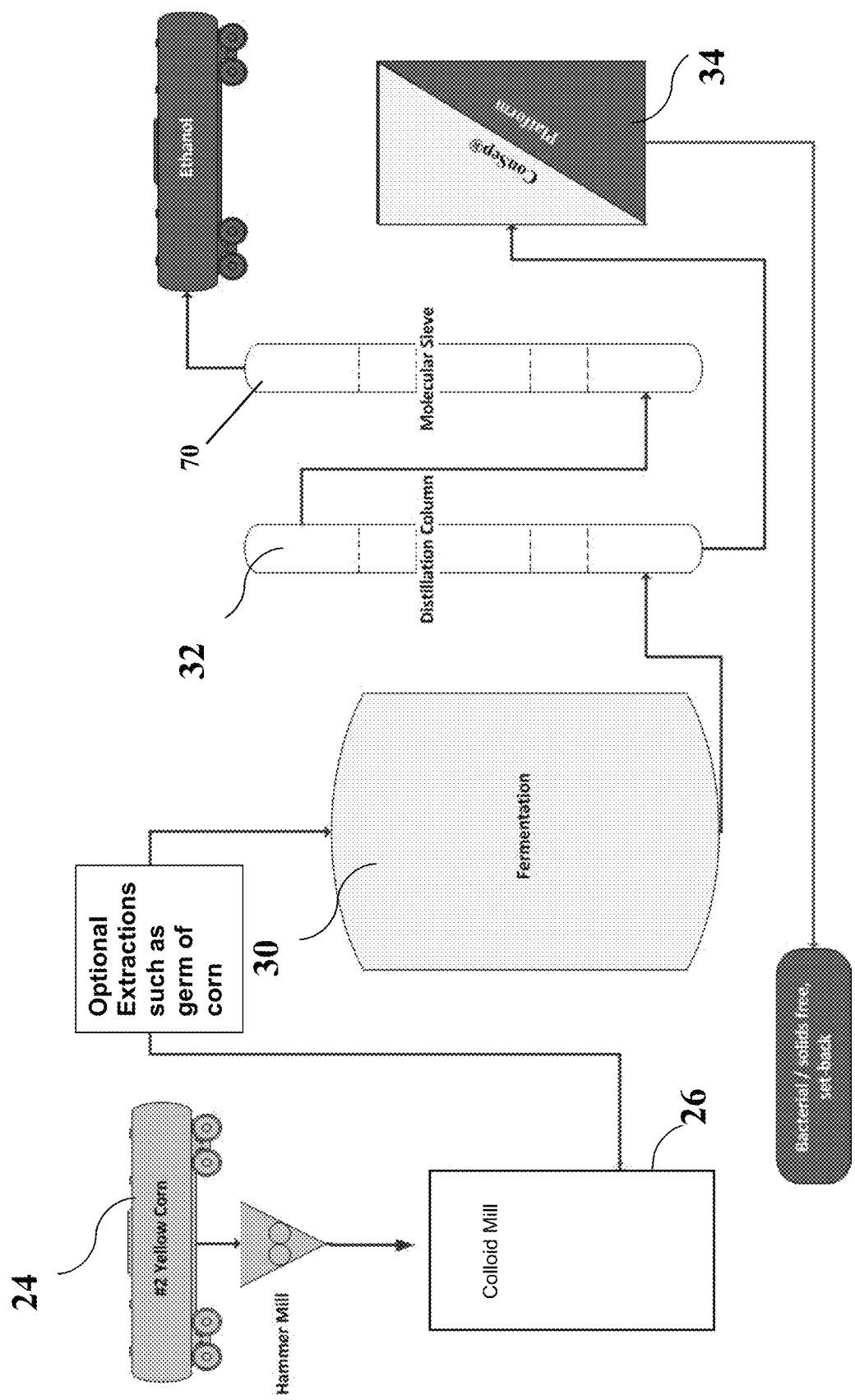
FIG. 4 shows a system that includes the addition of a particle reduction system to ensure optimal particle size for extraction of desired hydrocarbon molecules.

FIG. 4 shows an alternative set-up for extraction of ethanol. This system includes a colloid mill 26 to provide for reduction of particle size of the corn source material 24 or any other sugar or cellulose containing material. The colloid mill has the ability to grind the corn to manageable sizes and easier removal of desired products. Although this system shows yellow corn, other materials may be used such as corn stalks, tree material, plant material, cellulose waste, etc. Optionally, certain valuable products may be removed before forwarding to the fermentation vessel 30, such as the whole germ from the corn kernel wherein such extracted whole germ can be used in an extraction process for the removal of corn oil. The ground material is introduced into the fermentation vessel 30 along with necessary microbes for conversion of sugar molecules to ethanol and/or enzymes to break complex cellulose into simple sugars such as glucose and followed by fermentation and subsequent distillation in a distillation column 32. The bottom layer in the distillation column is directed to a cross-flow filtration cassette 34 of the present invention for separation of solids and providing for a thin n which can be further separated to remove proteins and other components. Any remaining wet paste may be used as animal feed.

Figure 5:
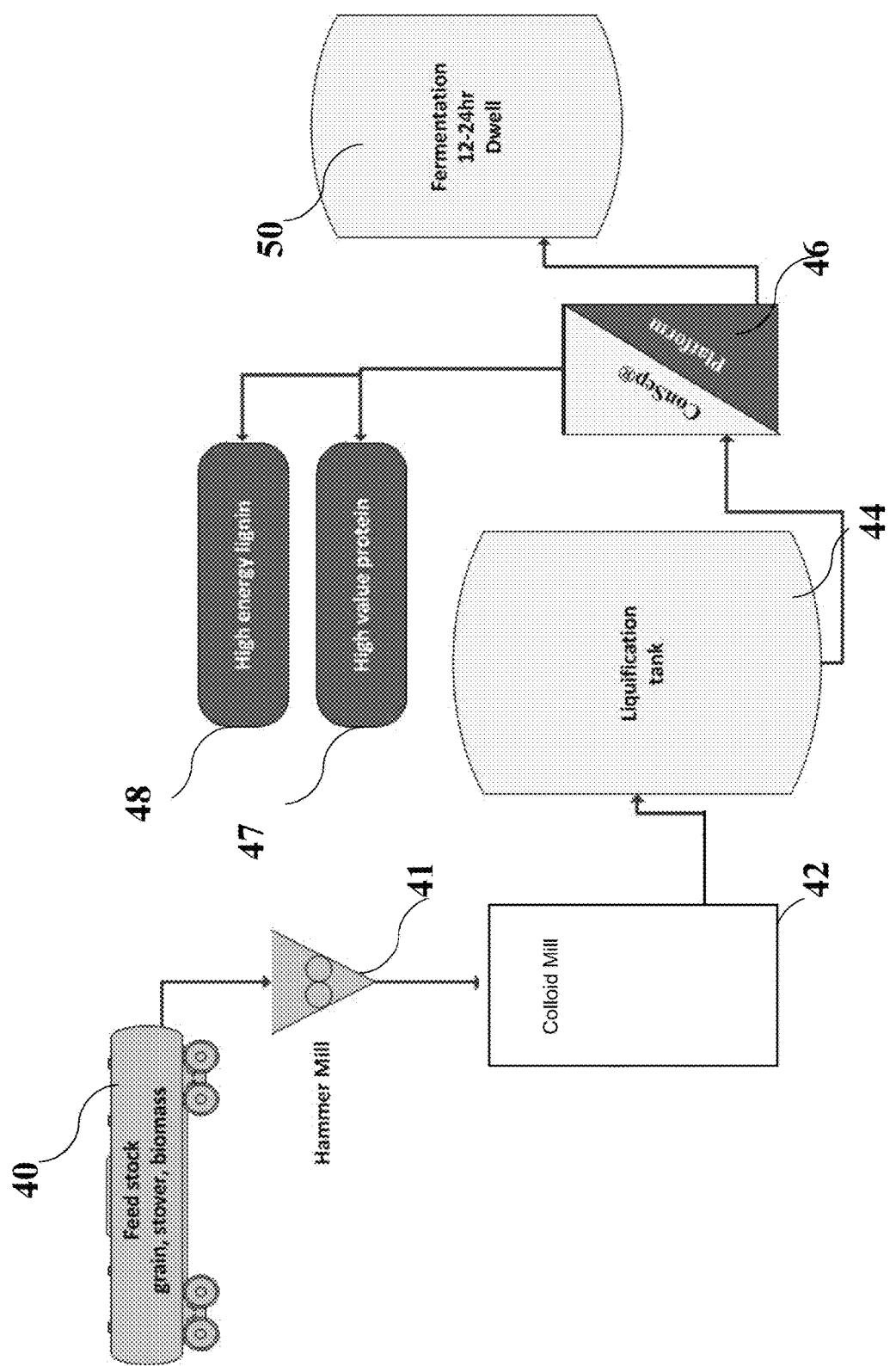
FIG. 5 shows stages of grinding of a source material, such as grains or biomass, and movement of same to a liquification tank wherein liquefying chemicals can be added for treatment of the source material for further separation of proteins and lignins from the source material and subsequent movement of the source material to a fermentation vessel.

FIG. 5 provides for a system used in dry-grain ethanol production wherein feed stock grain, stover, or biomass 40 is processed in a hammer 41 and the colloid mill 42 and introduced into a liquification tank 44 for breakdown of any lignocellulose type products. Lignocellulose is a structural material that comprises much of the mass of plants and composed mainly of cellulose, hemicellulose and lignin. Corn stover, switchgrass, miscanthus, wine pomace, sugarcane bagasse, municipal solid waste, woodchips and the byproducts of lawn and tree maintenance are some of the more popular cellulosic materials for ethanol production. Production of ethanol from lignocellulose has the advantage of abundant and diverse raw material compared to sources like corn and cane sugars, but requires a greater amount of processing to make the sugar monomers available to the microorganisms that are typically used to produce ethanol by fermentation. Enzymes such as cellulase, xylanase, and hemicellulase can be used to convert agricultural residues such as corn stover, distiller grains, wheat straw and sugar cane bagasse and energy crops such as switch grass into fermentable sugars which may be used to produce cellulosic ethanol. The contents of the liquification tank is passed through the cross-flow filtration cassette of the present invention 46, wherein hydrolyzates, such as proteins 47 and lignins 48 are removed and the remaining contents moved into the fermentation vessel 50 for the enzymatic production of ethanol. The high energy lignin and proteins can be directed to other uses, including proteins to animal feed, yeast to other markets and the lignin can be used to replace petroleum requirements. The ethanol containing stream is introduced to a distillation column as shown in FIG. 4, wherein the ethanol is drawn off and the remaining solution can be reintroduced into the fermentation vessel or proceed for further processing. Importantly, the setback is free of solids, proteins and microbial contamination. Further, by removing all solids in the setback there is more room available for additional processed corn thereby increasing a continuous stream of product. With the particle size of the feedstock reduced to less than about 0.5 mm all the distiller grains can be concentrated to greater than about 30% solids. Thus, there is less need for centrifuge or evaporation to produce grain with less moisture. The system can be operated in both a batch and continuous mode.

Figure 6:
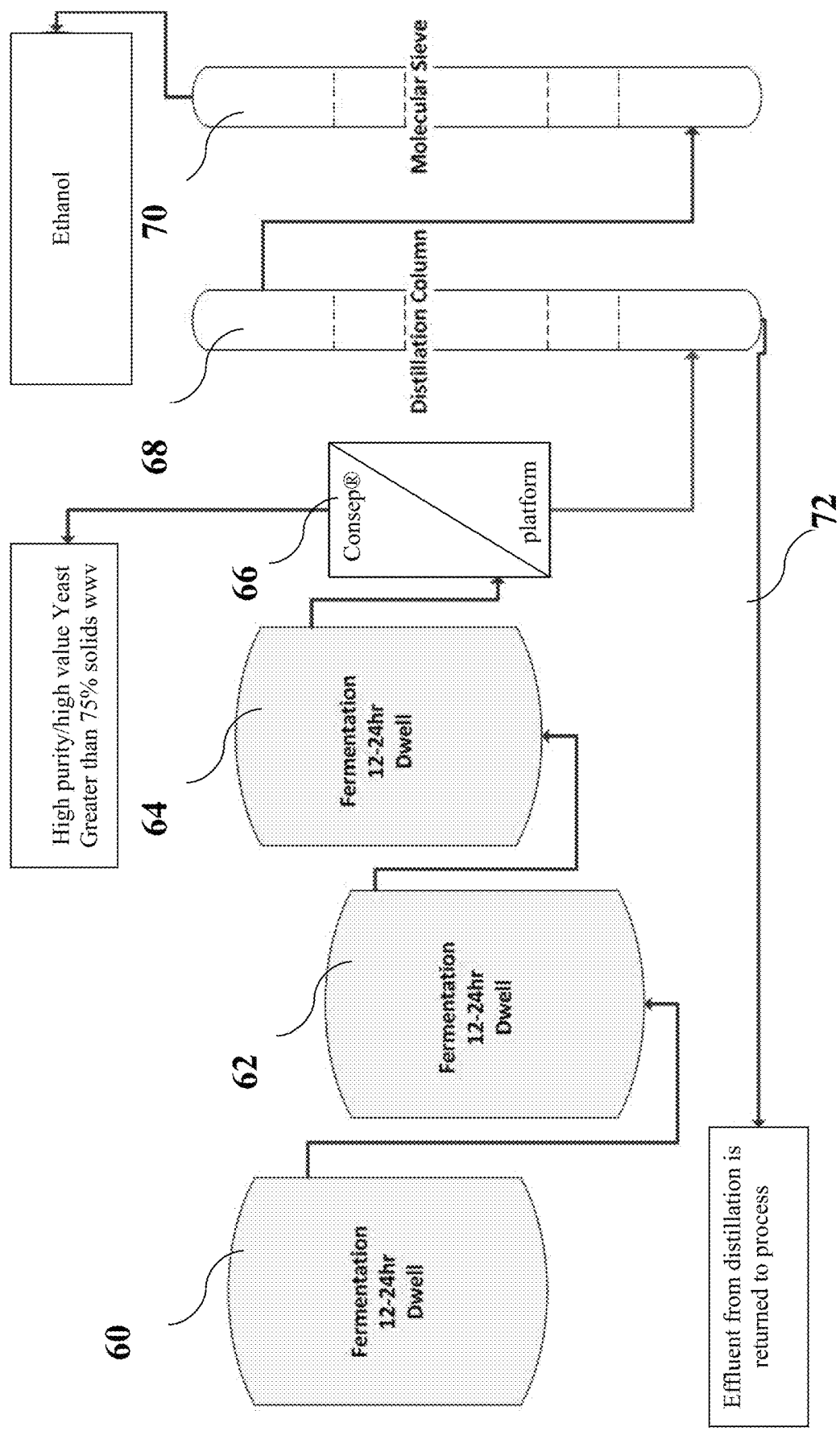
FIG. 6 shows an alternative set up for use of the cross-flow filtration cassette with multiple fermentation vessels in the separation of ethanol and the res use of yeast.

Placing reactor vessels and the cross-flow filtration cassettes in series or in parallel allows for optimal rates of substrate fermentation while permitting the minimization of total bioreactor size and the time required for production of the target product. The individual reactor vessels may be configured to operate at different fermentation cell mass concentrations or in different modes. For example, FIG. 6 shows downstream fermentation, distillation and recovery and also shows multiple fermentation vessels 60, 62 and 64 that can be used in the continuous biofuel production. Each vessel can be in a different mode, for example, one can be filling, one can be in the fermenting mode, and one can be emptying and resetting for the next batch. Further, as the fermentation medium is passed from one vessel to another, the concentration can be reduced by use of ultrafiltration membranes between the vessels. The fermentation medium, after passing through all the vessels, is passed through at least one cross-flow filtration cassette of the present invention 66 wherein the ethanol containing liquid is introduced to a distillation column 68 and wherein the ethanol is drawn off through a sieve 70. The remaining effluent solution 72 can be reintroduced into the fermentation vessel or proceed for further processing, such as processing of corn steep liquor or stillage.

Corn steep liquor is one of the byproducts of corn wet milling directed to the production of animal feed. It is also used as a nutrient for microorganisms in the production of enzymes, antibiotics, and other fermentation products. Corn steep liquor is a source of soluble proteins, amino acids, carbohydrates, organic acids, vitamins, and minerals and can be used as a source material. Importantly, corn steep liquor is highly viscous material but using the cross-flow filtration cassette of the present invention eliminates the need for centrifuge and traditional filtration. Other traditional filtration membranes, such as turbulence inducing screen channels cannot handle the processing of such thick solutions. The corn steep liquor can contain from about 15% to 25% solids and removal of liquid causes a wet distiller grain, also called a wet cake that contains from about 35% to 50% weight of solids.

Figure 7:
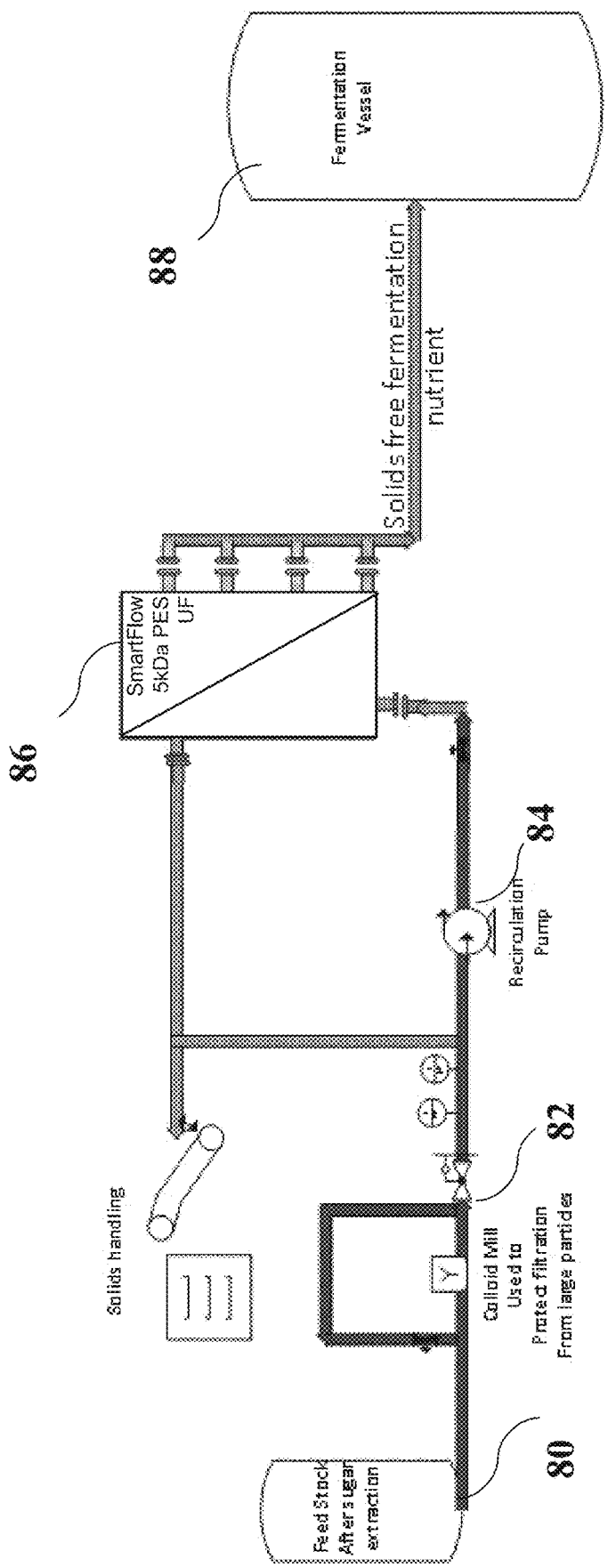
FIG. 7 shows a set-up for fermentation of a liquid that is devoid of solids.

FIG. 7 shows a system used for both upstream and downstream processing, wherein large particles from a feed stock 80 are reduced in any particle reduction system 82, thereby providing for a fairly consistent source material for further processing. Importantly the pump system 84 from the particle reduction system can be used as the primary pump mechanism for moving the source material through the cross-flow filtration cassette 86. The cross-flow filtration cassette provides for a permeate that is solid free but still contains the necessary nutrients for a fermentation process when supplied to the fermentation vessel 88. Thus, the nutrients added to the fermentor, which are free of solids, provides for increasing volumetric capacity by about 15 to 20%.

Ethanol producers are considering the use of corn stillage, a by-product of ethanol production, to generate renewable energy to offset fossil fuel cost and reduce the carbon intensity of the ethanol process. FIG. 6 shows that the at the bottom of the distillation column 68, any solids are removed including grain and added yeast as well as liquid added during the process. The thin stillage can be rerouted to the fermentation tank as make-up waste along line 72. In the present invention, it is envisioned that the thin stillage is concentrated by passing through a cross-flow filtration cassette of the present invention wherein additional water is removed thereby forming a concentrated stillage without the need of an evaporator. The concentrated syrup with a content of 30% to 60% of solids and which is high in proteins can be used either as a component in wet distiller grain for feeding to cattle or can be used as a feedstock in biogas production. For example, the thickened syrup may be added to a digester and produces methane. Interestingly, this methane gas can be used to power the ethanol process.

Figure 8:
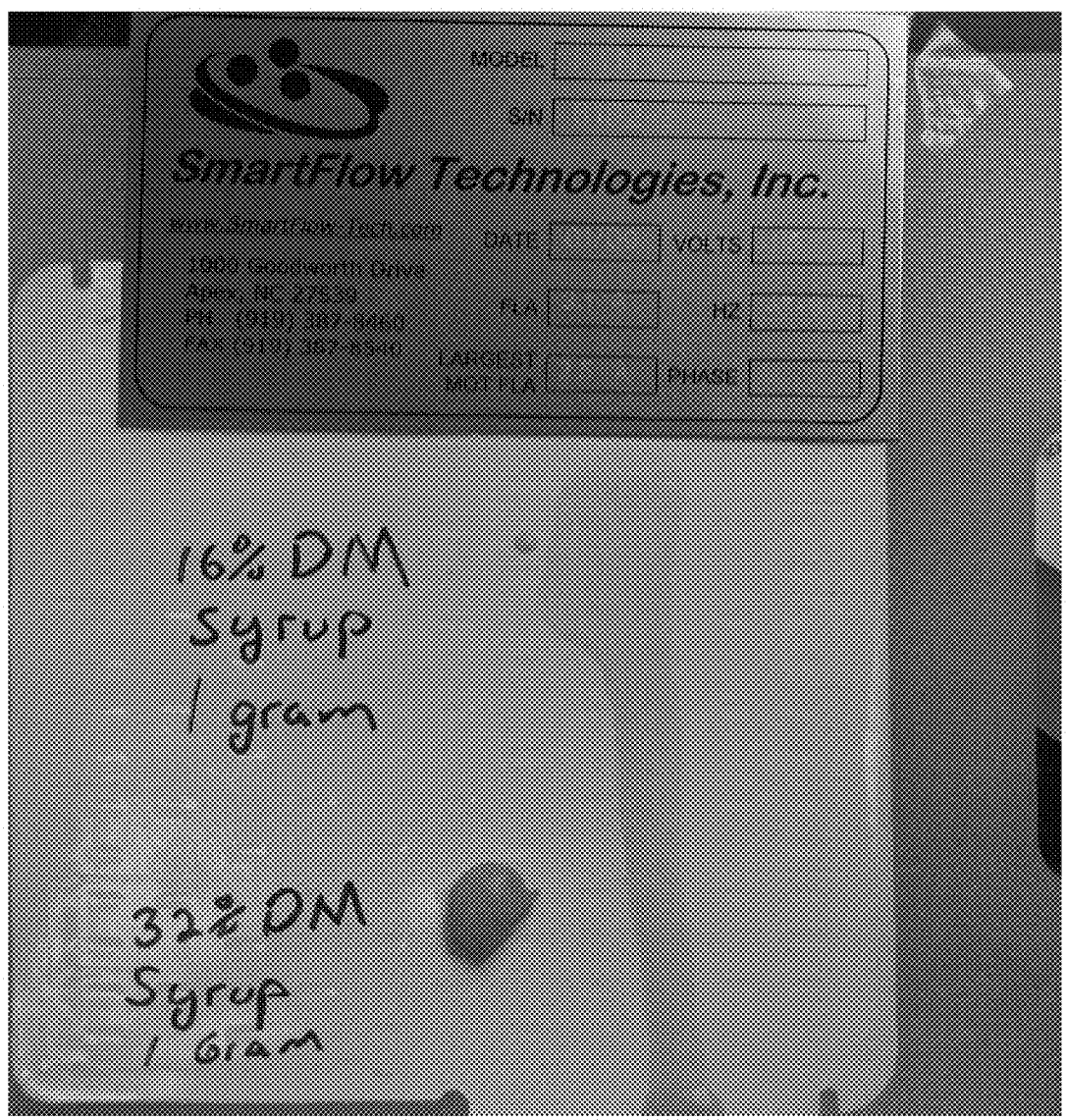
FIG. 8 shows the difference between stillage concentrations by the method of the present invention relative to that of evaporation.

FIG. 8 shows that using the cross-flow filtration cassette for concentrating the thin stillage cut provides for at least twice the amount of solids in the stillage and providing for increased concentration. As viewed in FIG. 8, the syrup with 32% solids showed an increase in solidity and no drainage on the vertical slab. This is in comparison to the thin stillage that passed through an evaporator and contained only 16% solids which means that it still include 86% liquid. Importantly, this increase in concentration provides for a higher value compound whether used in a biogas setup or feed to cattle.

Biogas systems may also use the cross-flow filtration cassettes of the present invention. Many farmer use methane digester to process farm waste, such as that involved with grain crops, seed, leaves, plants and dry or wet manure. The farm waste is processed in anaerobic digesters to derive methane biogas. The biogas is captured and the remaining biowaste (usually referred to as sludge and containing numerous nutrients) can be further concentrated by use of the cross-flow filtration cassettes of the present invention and then further processed for production of additional biofuels, such as ethanol and biobutanol. Nutrients can be removed including ammonia, phosphorus, potassium and other trace elements by use of the cross-flow filtration cassettes and that can be added to animal feed or reintroduced to soil as nutrients.

Figure 9:
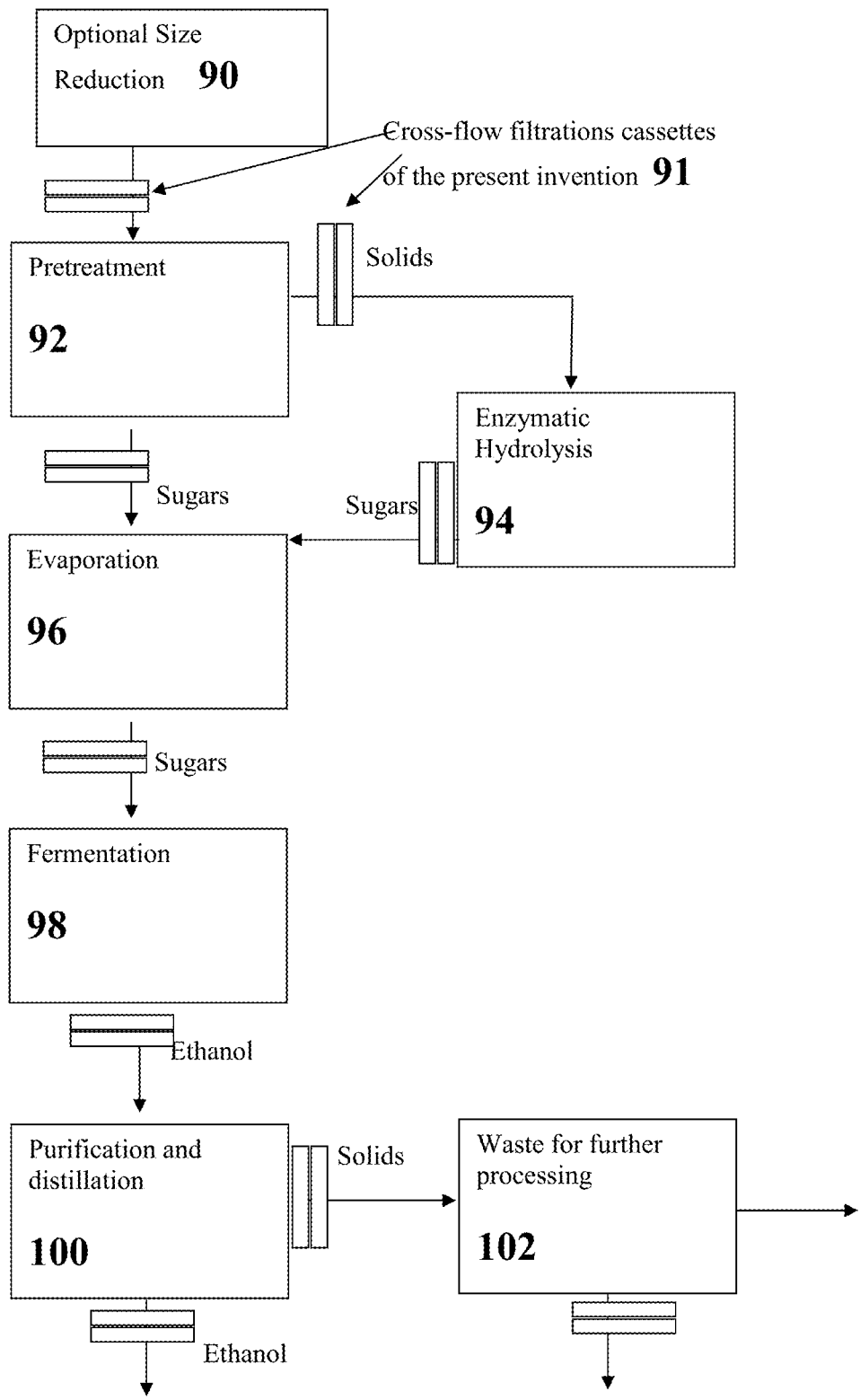
FIG. 9 shows a simplified flowsheet for ethanol production from lignocellulosic biomass including some of the possible placements of a cross-flow filtration cassette of the present invention.

FIG. 9 illustrates the steps for converting lignocellulose-to-ethanol. Initially, the biomass may be subjected to size reduction 90 by milling or chipping and the opening of the fibrous material for further treatment. The next step includes the pretreatment 92 for mobilization of the lignin and hemicellulose biopolymers. Sugars are collected either directly or from further breakage for enzymatic attack by hydrolysis of the polysaccharide matrix 94 to a sugar stream. The sugar stream can be concentrated by evaporation 96 to a level sufficient for a final ethanol concentration of at least 8.5%. The concentrated sugar material is fermented 98 and then subjected to further distillation and purification steps 100 to meet fuel specifications. The bottoms of the distillation process 102 are removed for further processing to provide additional desired products. All of the separation or purification processes use the cross-flow filtration cassettes 91 of the present invention.

That which is claimed is:

1. A method of producing renewable diesel fuel, comprising:
   (a) culturing a population of microorganisms selected from microalgae, oleaginous yeast or fungi, in the presence of a fixed carbon source, wherein: (i) the microorganisms accumulate at least 10% of their dry cell weight as lipid; and (ii) the fixed carbon source is selected from the group consisting of glycerol, depolymerized cellulosic material, sucrose, molasses, glucose, arabinose, galactose, xylose, fructose, mannose, acetate, and any combination of the foregoing;
   (b) isolating lipid from the cultured microorganisms using a cross-flow filtration cassette; and
   (c) subjecting the isolated lipids to one or more chemical reactions to generate straight chain alkanes, wherein renewable diesel is produced,
wherein the cross-flow filtration cassette comprises an array of sheet members of generally rectangular and generally planar shape, each having a top and a bottom surface, wherein the sheet members include in sequence in said array a first retentate sheet, a first filter sheet, a permeate sheet, a second filter sheet, and a second retentate sheet, wherein when a medium to be filtered flows across the filter sheets, solids or high-molecular-weight species of diameter larger than the filter sheet's pore size are retained in the retentate flow, and permeate species present in the medium diffuse through the filter sheets and enter the permeate sheet and permeate flow, wherein each of the sheet members in said array has at least one inlet basin opening at one end thereof, and at least one outlet basin opening at an opposite end thereof, with permeate passage openings at longitudinal side margin portions of the sheet members, wherein each of the first and second retentate sheets have a multiplicity of channel openings, extending longitudinally between the inlet and outlet basin openings of the sheets in the array, and the first retentate sheet and the second retentate sheet, respectively, are bonded to the first filter sheet and the second filter sheet about peripheral end and side portions thereof, and wherein, for each of the arrays, the inlet basin openings are in register with one another, the outlet basin openings are in register with one another, and the permeate passage openings are in register with one another, and the permeate passage openings of each of the retentate sheets are circumscribingly bonded to an adjacent filter sheet, with a central portion of each of the retentate sheets and adjacent filter sheets being unbonded to permit permeate contacting the retentate sheets to flow through the filter sheets to the permeate sheet.

* * * * *